(12) United States Patent
Wittenberger et al.

(10) Patent No.: US 7,981,110 B2
(45) Date of Patent: *Jul. 19, 2011

(54) SURGICAL CLAMP HAVING TRASMURALITY ASSESSMENT CAPABILITIES

(75) Inventors: Dan Wittenberger, Pierrefonds (CA); Daniel Nahon, Ottawa (CA); Marwan Abboud, Pierrefonds (CA); Jean-Pierre Lalonde, Verdun (CA); Cristian Petre, Laval (CA); Réal Ste-Marie, Montréal (CA); Sean Carroll, Rancho Cucamonga, CA (US); Allan Skanes, London (CA); Alan H. Menkis, London (CA)

(73) Assignee: Medtronic Cryocath LP, Toronto, Ontario (CA)

( * ) Notice: Subject to any disclaimer, the term of this patent is extended or adjusted under 35 U.S.C. 154(b) by 1184 days.

This patent is subject to a terminal disclaimer.

(21) Appl. No.: 11/709,067

(22) Filed: Feb. 21, 2007

(65) Prior Publication Data

US 2007/0149962 A1 Jun. 28, 2007

Related U.S. Application Data

(63) Continuation of application No. 10/841,955, filed on May 7, 2004, now Pat. No. 7,819,860, which is a continuation-in-part of application No. 10/458,745, filed on Jun. 10, 2003, now Pat. No. 7,044,946.

(51) Int. Cl.
*A61B 18/02* (2006.01)
(52) U.S. Cl. .............................. 606/23; 606/21; 606/207
(58) Field of Classification Search .............. 606/20–26, 606/50–52, 205–207
See application file for complete search history.

(56) References Cited

U.S. PATENT DOCUMENTS

| | | | |
|---|---|---|---|
| 4,745,918 A | 5/1988 | Feucht | |
| 4,867,404 A | 9/1989 | Harrington et al. | |
| 4,873,973 A | 10/1989 | Hagen et al. | |
| 5,071,430 A | 12/1991 | de Salis et al. | |
| 5,078,713 A | 1/1992 | Varney | |
| 5,304,183 A | 4/1994 | Gourlay et al. | |
| 5,443,463 A | 8/1995 | Stern et al. | |
| 5,496,312 A | 3/1996 | Klicek | |
| 5,536,267 A | 7/1996 | Edwards et al. | |

(Continued)

FOREIGN PATENT DOCUMENTS

CA 2482416 4/1999

(Continued)

OTHER PUBLICATIONS

Riemersa, D.J., et al., The Cryo-Jaw, A Clamp Designed for In Vitro Rheology Studies of Horse Digital Flexor Tendons, J. *Biomechanics*, vol. 15, No. 8, pp. 619-620, 1982.

(Continued)

*Primary Examiner* — Michael Peffley
(74) *Attorney, Agent, or Firm* — Christopher & Weisberg, P.A.

(57) ABSTRACT

A medical device is provided having a means for actuating a pair of opposing jaw members. The jaw members are movable relative to one another from a first position, wherein the jaw members are disposed in a spaced apart relation relative to one another, to a second position, wherein the jaw members cooperate to grasp tissue therebetween. An ablation mechanism is connected to at least one of the jaws members, such that the jaw members are capable of conducting ablation energy through the tissue grasped therebetween.

29 Claims, 15 Drawing Sheets

U.S. PATENT DOCUMENTS

| | | | |
|---|---|---|---|
| 5,565,122 A | 10/1996 | Zinnbauer et al. | |
| 5,733,280 A | 3/1998 | Avitall | |
| 5,762,069 A | 6/1998 | Kelleher et al. | |
| 5,860,970 A | 1/1999 | Goddard et al. | |
| 5,904,711 A | 5/1999 | Flom et al. | |
| 5,910,104 A * | 6/1999 | Dobak et al. | 600/121 |
| 5,992,158 A | 11/1999 | Goddard et al. | |
| 6,039,733 A | 3/2000 | Buysse et al. | |
| 6,063,050 A | 5/2000 | Manna et al. | |
| 6,071,303 A | 6/2000 | Laufer | |
| 6,083,223 A | 7/2000 | Baker | |
| 6,096,037 A | 8/2000 | Mulier et al. | |
| 6,102,909 A | 8/2000 | Chen et al. | |
| 6,139,563 A | 10/2000 | Cosgrove, III et al. | |
| 6,142,994 A | 11/2000 | Swanson et al. | |
| 6,146,378 A * | 11/2000 | Mikus et al. | 606/21 |
| 6,152,920 A | 11/2000 | Thompson et al. | |
| 6,161,543 A | 12/2000 | Cox et al. | |
| 6,174,309 B1 | 1/2001 | Wrublewski et al. | |
| 6,179,834 B1 | 1/2001 | Buysee et al. | |
| 6,187,003 B1 | 2/2001 | Buysee et al. | |
| 6,206,877 B1 | 3/2001 | Kese et al. | |
| 6,217,528 B1 | 4/2001 | Koblish et al. | |
| 6,237,605 B1 | 5/2001 | Vaska et al. | |
| 6,319,248 B1 | 11/2001 | Nahon | |
| 6,352,536 B1 | 3/2002 | Buysee et al. | |
| 6,375,652 B1 * | 4/2002 | Griswold | 606/20 |
| 6,383,181 B1 * | 5/2002 | Johnston et al. | 606/24 |
| 6,517,536 B2 | 2/2003 | Hooven et al. | |
| 6,527,767 B2 | 3/2003 | Wang et al. | |
| 6,544,274 B2 | 4/2003 | Danitz et al. | |
| 6,546,935 B2 | 4/2003 | Hooven | |
| 6,547,784 B1 * | 4/2003 | Thompson et al. | 606/21 |
| 6,666,858 B2 * | 12/2003 | Lafontaine | 606/21 |
| 6,699,240 B2 | 3/2004 | Francischelli | |
| 6,706,037 B2 * | 3/2004 | Zvuloni et al. | 606/21 |
| 6,767,346 B2 * | 7/2004 | Damasco et al. | 606/21 |
| 6,889,694 B2 | 5/2005 | Hooven | |
| 6,923,806 B2 | 8/2005 | Hooven et al. | |
| 6,926,712 B2 | 8/2005 | Phan | |
| 2001/0031961 A1 | 10/2001 | Hooven | |
| 2002/0015996 A1 | 2/2002 | Blumenfeld et al. | |
| 2002/0052602 A1 | 5/2002 | Wang | |
| 2002/0082593 A1 | 6/2002 | Hareyama et al. | |
| 2002/0091384 A1 | 7/2002 | Hooven et al. | |
| 2002/0103484 A1 | 8/2002 | Hooven | |
| 2002/0107513 A1 | 8/2002 | Hooven | |
| 2002/0107514 A1 | 8/2002 | Hooven | |
| 2002/0115993 A1 | 8/2002 | Hooven | |
| 2002/0120267 A1 | 8/2002 | Phan | |
| 2002/0120316 A1 | 8/2002 | Hooven et al. | |
| 2002/0143346 A1 | 10/2002 | McGuckin, Jr. et al. | |
| 2002/0177845 A1 | 11/2002 | Heiner et al. | |
| 2003/0004507 A1 | 1/2003 | Francischelli et al. | |
| 2003/0018331 A1 | 1/2003 | Dycus et al. | |
| 2003/0024537 A1 | 2/2003 | Cox et al. | |
| 2003/0032952 A1 | 2/2003 | Hooven | |
| 2003/0069572 A1 | 4/2003 | Wellman et al. | |
| 2003/0093068 A1 | 5/2003 | Hooven | |
| 2003/0120268 A1 | 6/2003 | Bertolero et al. | |
| 2003/0125729 A1 | 7/2003 | Hooven et al. | |
| 2004/0068274 A1 | 4/2004 | Hooven | |
| 2004/0073206 A1 | 4/2004 | Foley et al. | |

FOREIGN PATENT DOCUMENTS

| | | |
|---|---|---|
| CA | 2407645 A1 | 1/2001 |
| WO | 0182810 A1 | 11/2001 |

OTHER PUBLICATIONS

Patwardhan, A.M., et al., Intraoperative Radiofrequency Micropbipolar Coagulation to Replace Incisions of Maze III Procedure for Correcting Atrial Fibrillation in Patients with Rheumatic Valvular Disease, *European Journal of Cardio-Thoracic Surgery*, 12 (1997) 627 633.

Sjhattock, M.J., et al., A Cryoclamp for the Rapid Cryofixation of the Isolated Blood-Perfused Rabbit Cardia Papillary Muscle Preparation at Predefined times During the Contraction Cycle, *Journal of Microscopy*, vol. 192, Pt. 3, pp. 269-279, Dec. 1998.

Saltman, A.E., et al., A Completely Endoscopic Approach to Microwave Ablation for Atrial Fibrillation, *The Heart Surgery Forum*, #2003-11333, vol. 6, Issue (3), Jan. 13, 2003, pp. E38-E41.

Hamner, C.E., et al., Irrigated Bipolar Radiofrequency Ablation with Transmurality Feedback for the Surgical Cox-Maze Procedure, *The Heart Surgery Forum*, #2003-11770, vol. 6, Issue (5), Mar. 2003, pp. 418-423.

Gillinov, A.M., et al., Atricure Bipolar Radiofrequency Clamp for Intraoperative Ablation of Atrial Fibrillation, *The Annals of Thoracic Surgery*, 2002;74:2165-2168.

\* cited by examiner

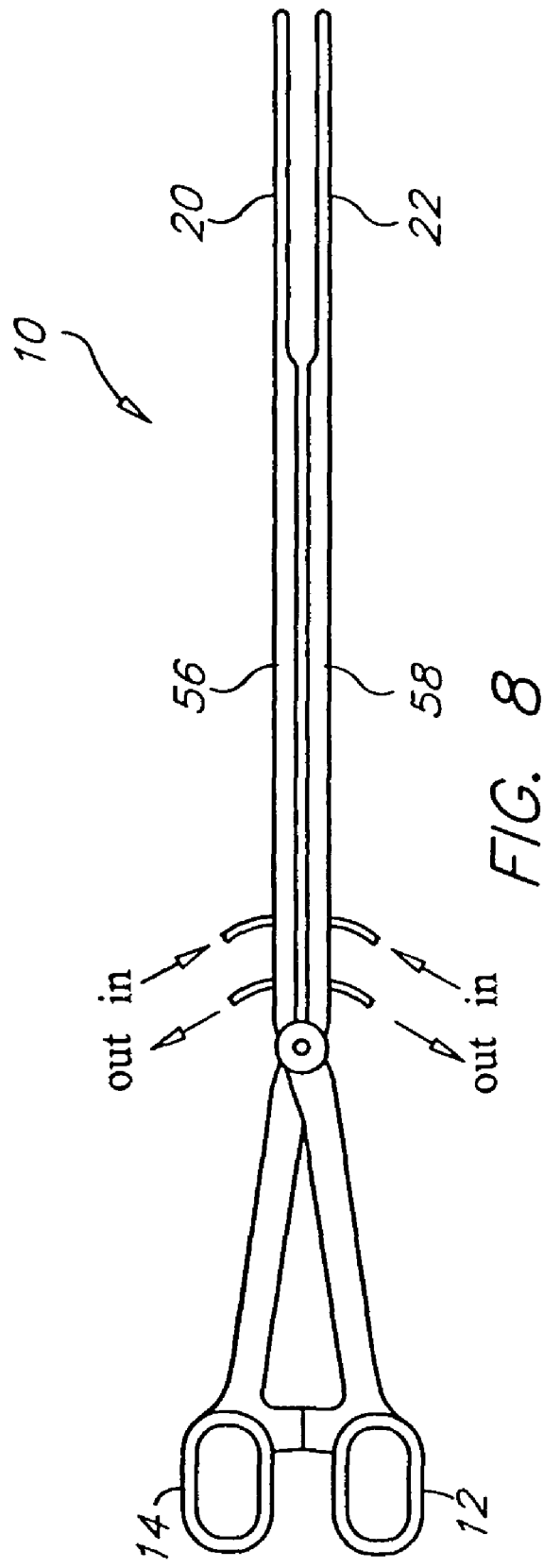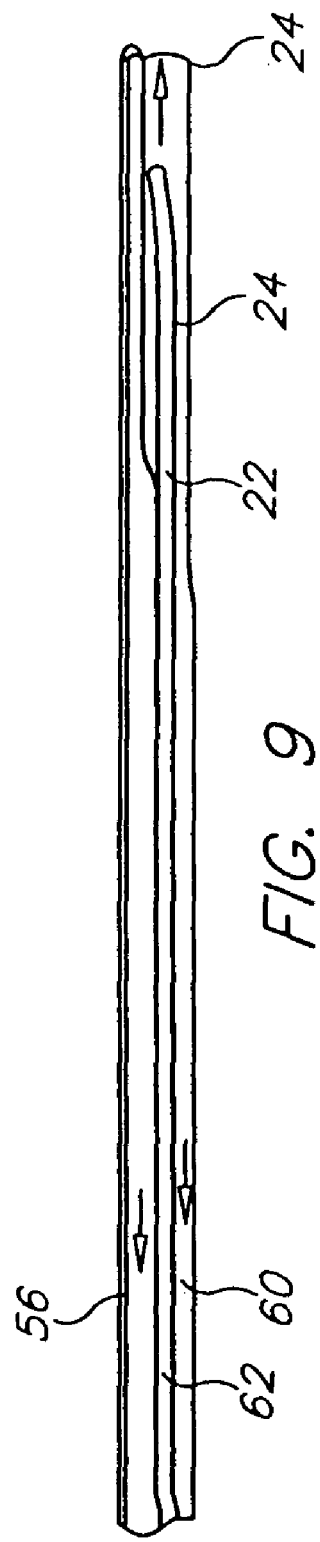
FIG. 8
FIG. 9

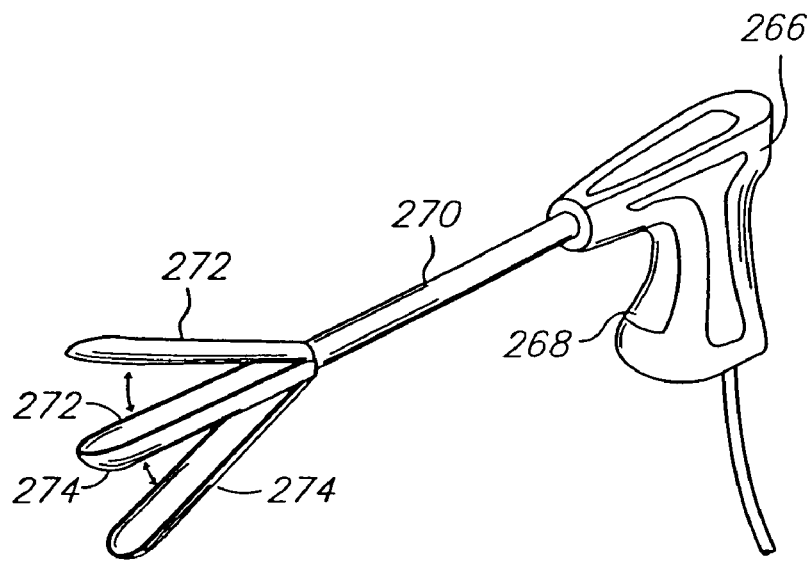
FIG. 18
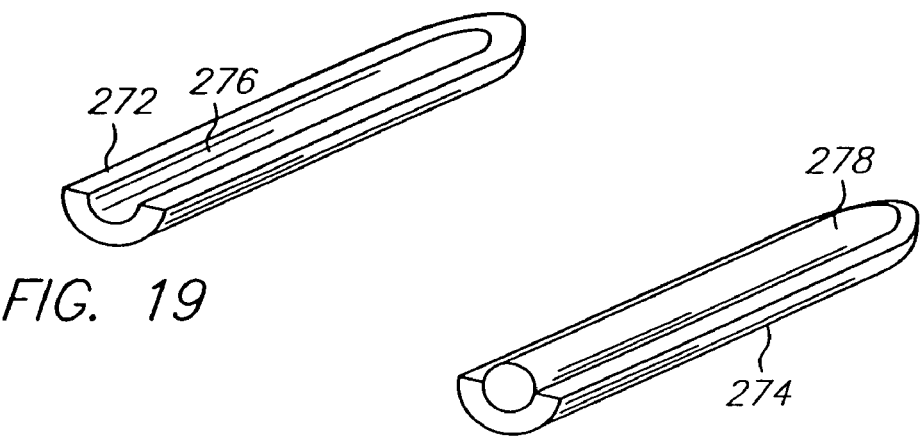
FIG. 19
FIG. 20

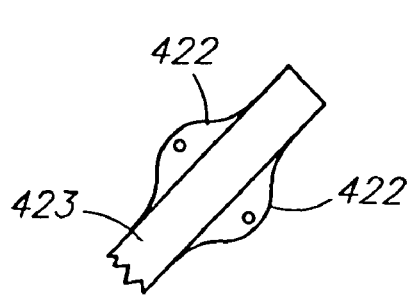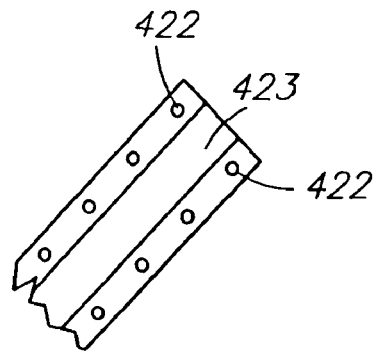
FIG. 26A    FIG. 26B
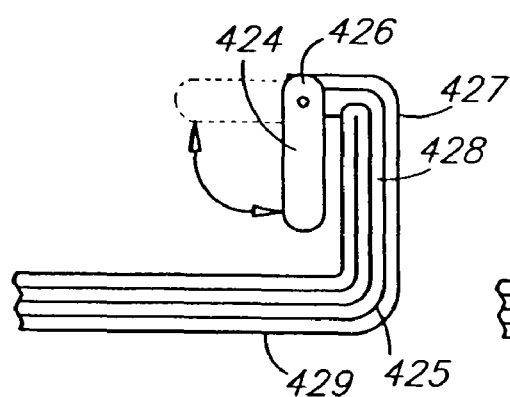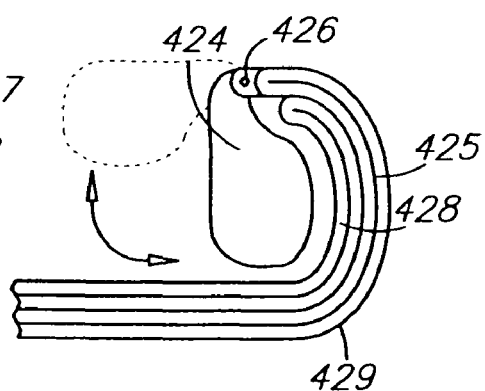
FIG. 27    FIG. 28
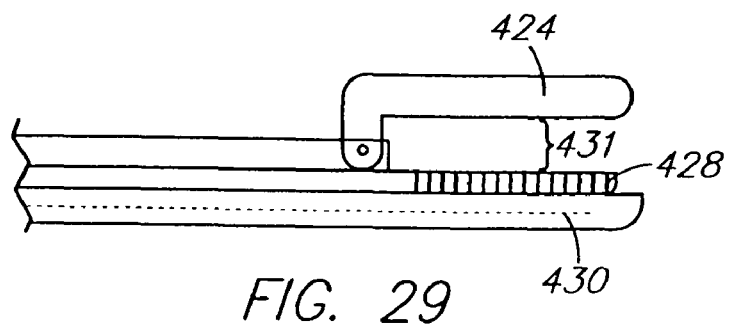
FIG. 29

SURGICAL CLAMP HAVING TRASMURALITY ASSESSMENT CAPABILITIES

CROSS-REFERENCE TO RELATED APPLICATION

This application is a continuation of U.S. patent application Ser. No. 10/841,955, filed May 7, 2004 and now U.S. Pat. No. 7,819,860, which application is a continuation-in-part of U.S. patent application Ser. No. 10/458,745, filed Jun. 10, 2003, now U.S. Pat. No. 7,044,946, the entirety of all of which are incorporated herein by reference.

STATEMENT REGARDING FEDERALLY SPONSORED RESEARCH OR DEVELOPMENT n/a

FIELD OF THE INVENTION

The present invention relates to a method and system for ablating tissue, and more particularly to a medical device having a pair of opposing jaws used for tissue ablation.

BACKGROUND OF THE INVENTION

It is well documented that atrial fibrillation (AF), either alone or as a consequence of other cardiac disease, continues to persist as the most common type of cardiac arrhythmia. In the United States, AF currently affects an estimated two million people, with approximately 160,000 new cases being diagnosed each year. The cost of treatment for AF alone is estimated to be in excess of $400 million worldwide each year.

Although pharmacological treatment is available for AF, the treatment is far from perfect. For example, certain antiarrhythmic drugs, like quinidine and procainamide, can reduce both the incidence and the duration of AF episodes. Yet, these drugs often fail to maintain sinus rhythm in the patient. Cardioactive drugs, like digitalis, Beta blockers, and calcium channel blockers, can also be given to control AF by restoring the heart's natural rhythm and limiting the natural clotting mechanism of the blood. However, antiarrhythmic drug therapy often becomes less effective over time. In addition, antiarrhythmic drug can have severe side effects, including pulmonary fibrosis and impaired liver function.

Another therapy for AF is surgery. In a technique known as the "Maze" procedure, a surgeon makes several incisions through the wall of the atrium with a scalpel and then sews the cuts back together, creating a scar pattern. The scars isolate and contain the chaotic electrical impulses to control and channel the electrical signals. The Maze procedure is expensive, complicated to perform, and associated with long hospital stays and high morbidity.

An alternative to open heart or open chest surgery is a minimally invasive treatment in which ablation devices are used to form scars in various locations in the atrial tissue. Ablation devices that apply heat or cold to body tissue are known. Typically, these devices have an elongate, highly-flexible shaft with a steerable distal end for negotiating a path through the body of a patient. Rigid shaft devices are used in more invasive procedures where a more local opening or direct access to a treatment site is available or created.

It is important to note that these devices are used in an attempt to ablate tissue through the full thickness of the cardiac wall, and thus create a risk associated with damaging structures within or on the outer surface of the cardiac wall. Accordingly ablation devices have been developed which include opposing jaw members to ablate tissue from both sides of the cardiac wall. For example, U.S. Pat. No. 6,161,543 to Cox; U.S. Pat. No. 5,733,280 to Avitall; and U.S. Pat. No. 6,517,536 to Hooven describe techniques for ablating tissue of organs or vessels having opposing walls and disclose ablation devices having clamping members to clamp a treatment site therebetween. Such devices include rigid members/shafts to facilitate reaching the tissue treatment site.

While rigid shafts may be useful in some applications, they have certain limitations as well. For example, without a preset shape for reaching a particular location in the body of a patient, the rigid nature of the shaft limits the area of tissue that can be reached and treated. Even where a relatively large incision is provided, tissue areas that are not at least somewhat directly accessible cannot be reached.

Although a rigid shaft can be provided with a predetermined shape, one must select a device with a rigid shaft that has the most appropriate shape for positioning the working portion of the device in contact with the treatment site in view of the particular anatomical pathway to be followed in the patient. It will be appreciated that a large inventory of devices having rigid shafts may be required to accommodate the various treatment sites and patient anatomies. As an example, U.S. Pat. No. 6,161,543 to Cox et al. describes a variety of rigid probe shapes. Further, for a patient having a relatively uncommon anatomic configuration and/or a difficult to reach treatment site, all rigid devices of an existing set may have less than optimal shapes for positioning. This may impair the prospects of successfully carrying out the treatment procedure. For an ablation device which must bear against tissue at the remote region to create lesions, the contour followed by the device in reaching the target site will in general further restrict the direction and magnitude of the movement and forces which may be applied or exerted on the working portion of the device to effect tissue contact and treatment.

SUMMARY OF THE INVENTION

The present invention advantageously provides a surgical clamp having a pair of opposing jaw members that are movable relative to one another from a first position, wherein the jaw members are disposed in a spaced apart relation relative to one another, to a second position, wherein the jaw members cooperate to grasp tissue therebetween. An ablation tool is connected to at least one of the jaws members, such that the jaw members are capable of conducting ablation energy through the tissue grasped therebetween.

In an exemplary embodiment, a medical device for ablating tissue is provided, having a pair of opposing jaws positionable from a first position to a second position, at least one of the opposing jaws including an ablation element, and a shaft assembly operable connected to the opposing jaws. The shaft assembly has a malleability such that the shaft assembly retains a first shape until manipulated to a second shape.

In another embodiment, a medical device for ablating tissue is provided, including a first jaw and a second jaw, where the first jaw includes a first jaw ablation tool having at least one first jaw ablation segment. A shaft assembly is also provided. The shaft assembly is operably connected to the first jaw and the second jaw, and is malleable such that the shaft assembly retains a first shape until manipulated to a second shape. The medical device also includes a handle assembly that is attached to the shaft assembly opposite the first jaw and the second jaw. The handle assembly is operably connected to the first jaw and the second jaw to move the first jaw and the second jaw from a first position to a second position.

In yet another exemplary embodiment, a medical device for ablating tissue is provided having a first jaw and a second jaw, the first jaw including a first jaw ablation tool configured to circulate cryogenic fluid therethrough and having at least one first jaw ablation segment. Also included is a shaft assembly operably connected to the first jaw and the second jaw. The shaft assembly has malleability such that the shaft assembly retains a first shape until manipulated to a second shape. The medical device further includes a handle assembly attached to the shaft assembly opposite the first jaw and the second jaw, where the handle assembly is operably connected to the first jaw and the second jaw to move the first jaw and the second jaw from a first position to a second position. An ablation control system is operably connected to the first ablation tool.

In another exemplary embodiment, a medical device is provided having an elongated shaft, a cooling element, and a second element movable with respect to the cooling element to define a clamp, wherein the movable element is selectively detachable from the shaft.

In an exemplary method, a method of ablating tissue includes the steps of: providing an ablating device having a pair of opposing jaws positionable from a first position to a second position, where at least one of said opposing jaws includes an ablation tool and a shaft assembly operable connected to the opposing jaws, the shaft assembly having a malleability such that the shaft assembly retains a first shape until manipulated to a second shape; manipulating the shaft assembly from the first shape to the second shape; positioning the opposing jaws in the first position such that the opposing jaws are in a spaced apart relation; placing the opposing jaws about the tissue to be treated; positioning the opposing jaws in the second position such that the opposing jaws grasp the tissue to be treated; and ablating the tissue to be treated.

In another exemplary method, a method for evaluating transmurality of a lesion is provided and includes the steps of positioning a first and a second jaw of an ablating device about tissue to be treated; applying a cooling element to at least the first jaw of the ablating element; and measuring temperature from a temperature sensor associated with the second jaw of the ablating device.

In another exemplary embodiment, a medical device for evaluating transmurality of a lesion is provided including a shaft assembly having malleability such that the shaft assembly retains a first shape until manipulated to a second shape, a proximal jaw operably connected to the shaft assembly, a pair of sensors extending from the proximal jaw, and a handle assembly attached to the shaft assembly opposite the proximal jaw, the handle assembly being operably connected to the proximal jaw to move the pair of sensors from a first position to a second position proximate an ablation site.

In another exemplary embodiment, a medical device having ablation and transmurality assessment capabilities is provided having a malleable surgical clamp with transmurality capability, and a flexible ablation tool removably insertable within the surgical clamp.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 8 is a plan view of the surgical clamp of FIG. 1 including elongated shafts;

FIG. 9 is a sectional view of the elongated shaft and ablation segment of the surgical clamp of FIG. 8;

FIG. 18 illustrates still another surgical clamp configuration;

FIGS. 19 and 20 illustrate additional details of the jaw elements shown in FIG. 18.

FIGS. 26A and 26B illustrate two embodiments of a transmurality assessment mechanism disposed on a cryoprobe;

FIGS. 27 and 28 illustrate two embodiments of a hinged surgical clamp having active cryotreatment elements;

FIG. 29 illustrates an additional surgical clamp having a detachable passive jaw;

DETAILED DESCRIPTION OF THE INVENTION

The present invention provides a medical device having a handle assembly for actuating a pair of opposing jaw members. The jaw members are movable relative to one another from a first position, wherein the jaw members are disposed in a spaced apart relation relative to one another, to a second position, wherein the jaw members cooperate to grasp tissue therebetween. An ablation tool is connected to at least one of the jaw members, such that the jaw members are capable of conducting ablation energy through the tissue grasped therebetween.

Figure 1:
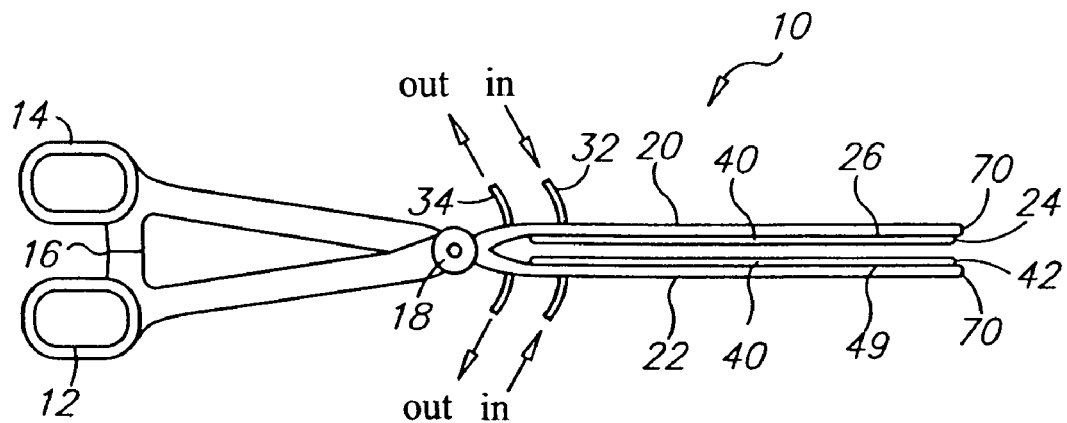
FIG. 1 is a plan view of a surgical clamp in accordance with the present invention.

Referring now to the figures in which like reference designators refer to like elements, there is shown in FIG. 1 a plan view of an exemplary embodiment of the medical device constructed in accordance with the principles of the present invention and designated generally as surgical clamp 10. The surgical clamp 10 includes a handle assembly having elongated handles 12 and 14 and may optionally include a lock mechanism 16, similar to a conventional surgical hemostat. The elongated handles 12, 14 are connected to one another by pivot or hinge 18, and continue distally in the form of a first elongated jaw 20 and a second elongated jaw 22. At least one of the elongated jaws 20, 22 includes an ablation tool. For example, the first elongated jaw 20 includes an ablation tool 24 positioned on the inner surface 26 of the first elongated jaw 20.

Figure 2:
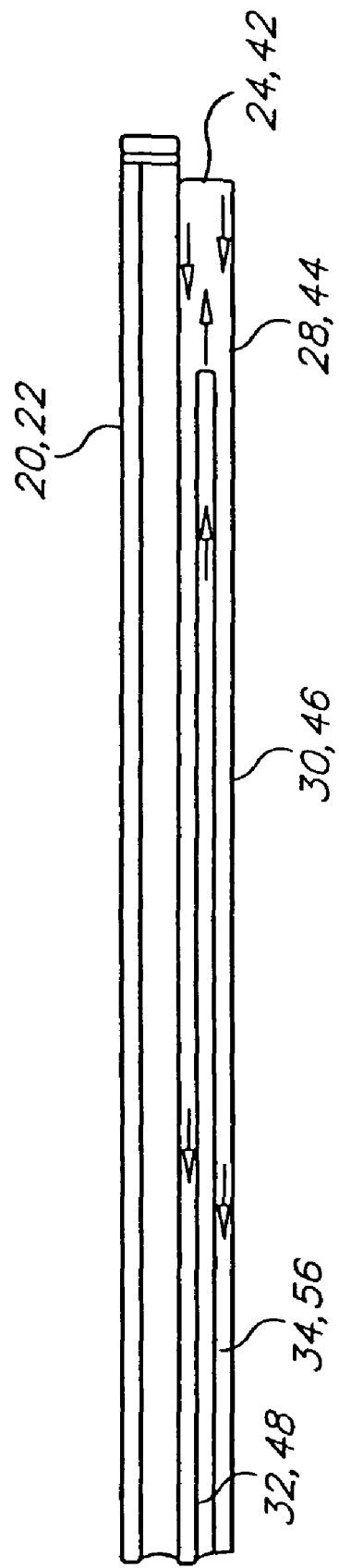
FIG. 2 is a sectional view of an ablation segment of the surgical clamp of FIG. 1.
Figure 3:
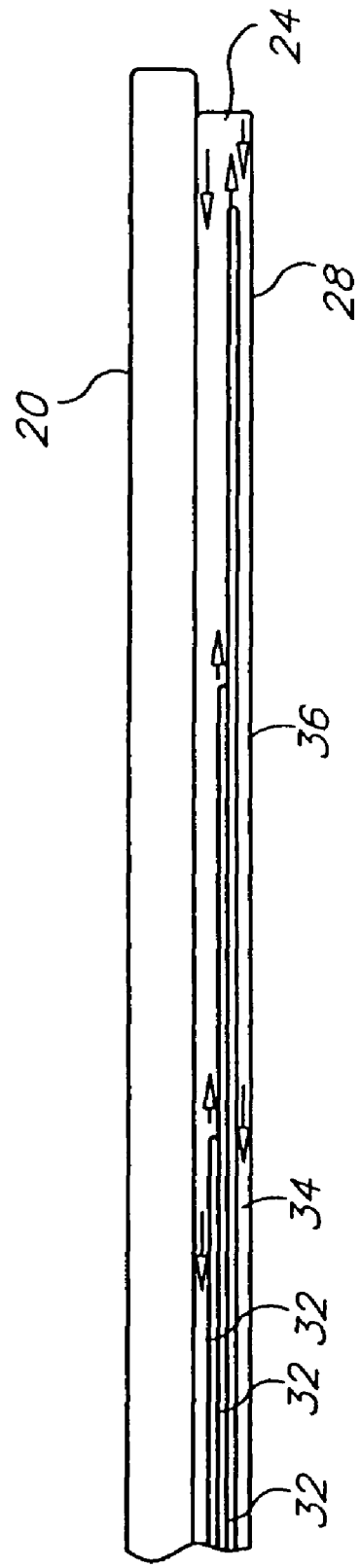
FIG. 3 is a sectional view of an ablation segment including multiple injection tubes of the surgical clamp of FIG. 1.

Referring to FIGS. 2-3, the ablation tool 24 includes an ablation segment 28 having a thermally-transmissive region 30, and defining a fluid path having at least one fluid inlet 32 and a fluid outlet 34 through the ablation tool 24 to the ablation segment 28, wherein the fluid inlet 32 is in fluid communication with a cryogenic fluid source. Also, even though many materials and structures can be thermally conductive or thermally transmissive if chilled to a very low temperature and/or cold soaked, as used herein, a "thermally-transmissive region" is intended to broadly encompass any structure or region of the ablation tool 24 that readily conducts heat.

For example, a metal structure exposed (directly or indirectly) to the cryogenic fluid path is considered a thermally-transmissive region 30 even if an adjacent polymeric or latex portion also permits heat transfer, but to a much lesser extent than the metal. Thus, the thermally-transmissive region 30 can be viewed as a relative term to compare the heat transfer characteristics of different catheter regions or structures, regardless of the material.

Furthermore, while the thermally-transmissive region 30 can include a single, continuous, and uninterrupted surface or structure, it can also include multiple, discrete, thermally-transmissive structures that collectively define a thermally-transmissive region that is elongate or linear. Depending on the ability of the cryogenic system, or portions thereof, to handle given thermal loads, the ablation of an elongate tissue path can be performed in a single or multiple cycle process with or without having to relocate the catheter one or more times or drag it across tissue.

Figure 4:
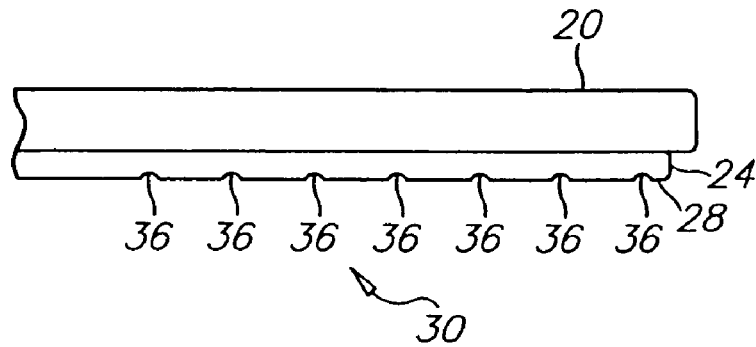
FIG. 4 is a sectional view of an ablation segment including orifices of the surgical clamp of FIG. 1.

In an exemplary embodiment, as shown in FIG. 4, the ablation segment 28 includes one or more orifices 36, where the orifices 36 define the thermally-transmissive region 30. The orifices 36 enable the application of cryogenic fluid directly onto the tissue to be treated.

Additionally, the second elongated jaw 22 can include an ablation tool 42 positioned on its inner surface. The ablation tool 42 includes an ablation segment 44 having a thermally-transmissive region 46, and defines a fluid path having at least one fluid inlet 48 and a fluid outlet 56 through the ablation tool 42 and the ablation segment 46, wherein the fluid inlet 48 is in fluid communication with a cryogenic fluid source.

Figure 5:
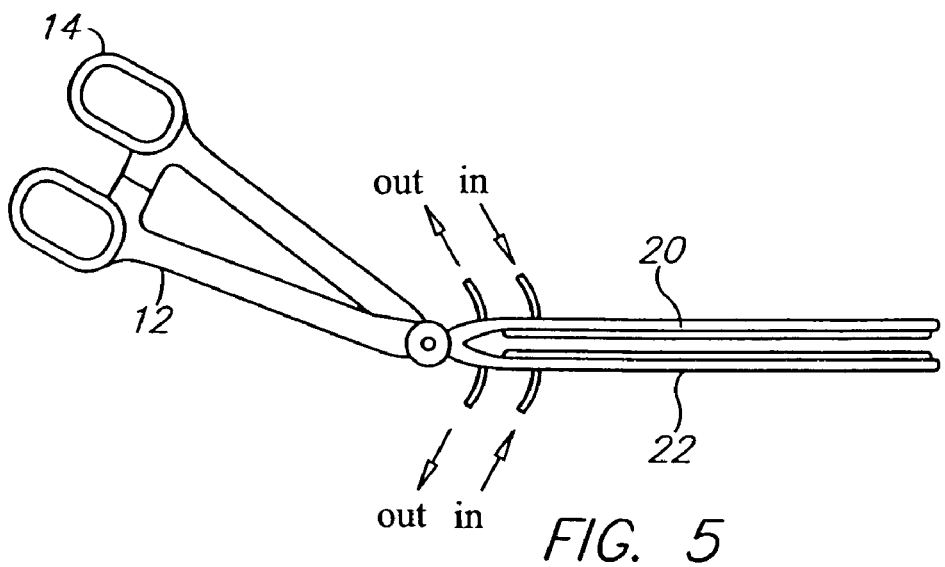
FIG. 5 is a plan view of an alternative embodiment of the surgical clamp of FIG. 1.

In an exemplary embodiment, as shown in FIG. 5, the handles 12 and 14 are at an acute angle to the first elongated jaw 20 and the second elongated jaw 22. Furthermore, as shown in FIG. 6, the first elongated jaw 20 and the second elongated jaw 22 include a curved portion.

Figure 6:
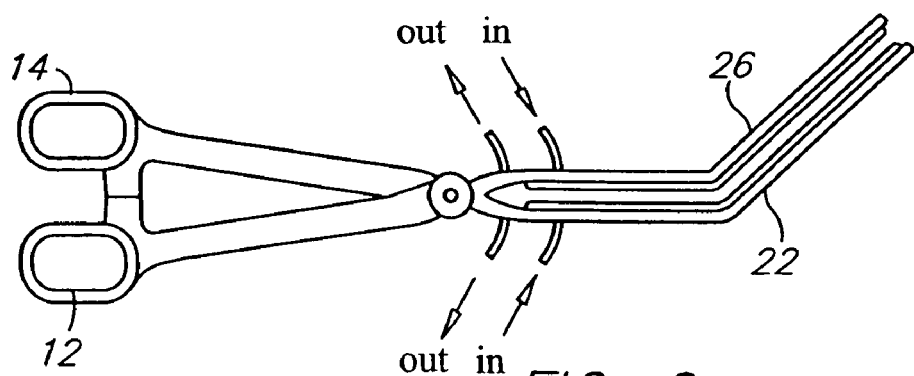
FIG. 6 is a plan view of the surgical clamp of FIG. 1 including curved jaws.

Each of FIGS. 1, 5, and 6 illustrate the various inlet ("in") and outlet ("out") ports for supplying and evacuating fluid to and from the jaws 20 and 22.

Additionally, the first elongated jaw 20 and the second elongated jaw 22 are malleable, each have a shape-holding deformability, that is, they have rigidity such that the first elongated jaw 20 and the second elongated jaw 22 each retain a first shape until manipulated to a further shape with the application of moderate pressure, and until reshaped. The first elongated jaw 20 and the second elongated jaw 22 retain their shape with sufficient rigidity to manipulate the ablation segment 28 against tissue, and push it past intervening tissue to a desired position.

It is understood that shape, as used herein, is to be construed broadly to include any contour which is needed to configure the first elongated jaw 20 and the second elongated jaw 22 for positioning the active or distal portion of the ablation tool 24, and may include successive bends or segments having more than one curve, angle, deformation or other non-linear configuration. The shape-retaining feature of the first elongated jaw 20 and the second elongated jaw 22 allows an operator to bend the first elongated jaw 20 and the second elongated jaw 22 to a shape or contour, for example around an organ or tissue structure, and have an optimal configuration for positioning and or orienting the active or distal region of the first elongated jaw 20 and the second elongated jaw 22 based upon the particular anatomy of a patient and the location of the treatment site.

Further, the stiffness of first elongated jaw 20 and the second elongated jaw 22 is such that the surgeon can form the first elongated jaw 20 and the second elongated jaw 22 by hand to a desired shape without undue effort, and yet the first elongated jaw 20 and the second elongated jaw 22 retain the set shape as the surgical clamp 10 is maneuvered to and held in position at the treatment site. The first elongated jaw 20 and the second elongated jaw 22 should also be sufficiently rigid such that the surgeon can place the ablation segment 28 of the ablation tool 24 in pressured contact with the tissue treatment site. That is, the first elongated jaw 20 and the second elongated jaw 22 are sufficiently stiff to enable the surgeon to press the ablation segment 28 against the tissue to be treated without inducing a further deformation in the shape of the first elongated jaw 20 and the second elongated jaw 22. The first elongated jaw 20 and the second elongated jaw 22 may in some embodiments deflect slightly, and yet have sufficient stiffness to transfer an effective level of lateral force at their distal end.

In an exemplary embodiment, the first elongated jaw 20 and the second elongated jaw 22 are configured so that they are deformable in a single plane, where the first elongated jaw 20 and the second elongated jaw 22 remain substantially rigid in all other planes. For example, the first elongated jaw 20 and the second elongated jaw 22 can be manipulated in a first plane from a first shape to a second shape, wherein the first elongated jaw 20 and the second elongated jaw 22 are sufficiently rigid to retain the second shape. The first elongated jaw 20 and the second elongated jaw 22 also have sufficient rigidity such that the first elongated jaw 20 and the second elongated jaw 22 cannot be manipulated in a second plane orthogonal to the first plane, such that the first elongated jaw 20 and the second elongated jaw 22 are deformable only in the first plane. As such, the first elongated jaw 20 and the second elongated jaw 22 are deformable in only one plane.

Figure 7:
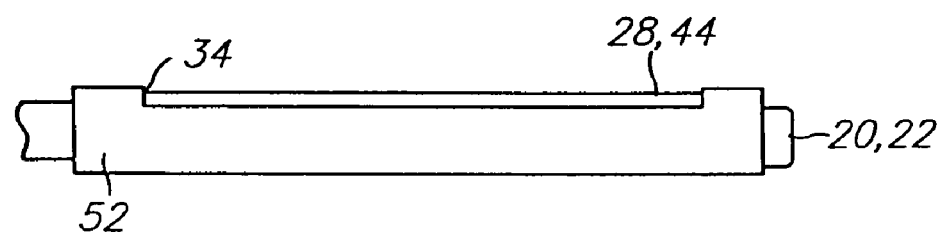
FIG. 7 is a sectional view of an ablation segment including insulation sleeve of the surgical clamp of FIG. 1

In accordance with yet another aspect of the invention, as shown in FIG. 7, particularly directed to the ablative properties of ablation segments 28, 44, the energy distribution during treatment of tissue is further controlled by an adjustable insulation sleeve 52, wherein one each extends over and partially envelops the ablation segments 28, 44. A slotted segment in the insulation sleeve 52 forms a partial circumferential blanket or insulating sleeve which prevents the ablation segments 28, 44 from affecting tissue on one side of the ablation segments 28, 44, while leaving the other side of the ablation segments 28, 44 exposed for contact with tissue.

In a further exemplary embodiment, as shown in FIG. 8, the surgical clamp 10 includes a shaft assembly having a first shaft 56 and a second shaft 58 interposed between the handles 12 and 14 and the first elongated jaw 20 and the second elongated jaw 22. The first shaft 56 and a second shaft 58 operably connect the first elongated jaw 20 and the second elongated jaw 22 to the handles 12 and 14 such that the first elongated jaw 20 and the second elongated jaw 22 are movable relative to one another from a first position, wherein the first elongated jaw 22 and the second elongated jaw 20 are disposed in a spaced apart relation relative to one another, to a second position, wherein the first elongated jaw 20 and the second elongated jaw 22 cooperate to grasp tissue therebetween.

Referring to FIG. 9, the first shaft 56 is substantially hollow, defining a first lumen 60 having at least one input lumen 62 positioned therein, wherein the first lumen 60 and the at least one lumen 62 define a fluid path to the ablation tool 24 on the first elongated jaw 20. The first lumen 60 and the at least one lumen 62 are in fluid communication with the ablation fluid outlet 34 and the ablation fluid inlet 32.

Additionally, similar to the first shaft 56, the second shaft 58 can be substantially hollow, defining a first lumen having at least one input lumen positioned therein, wherein the first lumen 60 and the at least one lumen 62 define a fluid path to the ablation tool 42 on the second elongated jaw 22. The first lumen and the at least one lumen 62 are in fluid communication with the ablation fluid outlet 56 and the ablation fluid inlet 48.

The first shaft 56 and the second shaft 58 are malleable, each have a shape-holding deformability, that is, they have a rigidity such that the first shaft 56 and the second shaft 58 each retain a first shape until manipulated to a further shape with the application of moderate pressure, and until reshaped. The first shaft 56 and the second shaft 58 retain their shape with sufficient rigidity to close the first elongated jaw 20 and the second elongated jaw 22 to grasp the tissue, and push it past intervening tissue to a desired position.

It is understood that shape, as used herein, is to be construed broadly to include any contour which is needed to configure the surgical clamp 10 for positioning the active or distal portion of the ablation tool 24, and may include successive bends or segments having more than one curve, angle, deformation or other non-linear configuration. The shape-retaining feature of the first shaft 56 and the second shaft 58 allows an operator to bend the first shaft 56 and the second shaft 58 to a shape or contour, for example around an organ or tissue structure, and have an optimal configuration for positioning and or orienting the active or distal region of the surgical clamp 10 based upon the particular anatomy of a patient and the location of the treatment site.

Further, the stiffness of the first shaft 56 and the second shaft 58 is such that the surgeon can form the first shaft 56 and the second shaft 58 by hand to a desired shape without undue effort, and yet the first shaft 56 and the second shaft 58 retain the set shape as the surgical clamp 10 is maneuvered to and held in position at the treatment site. The first shaft 56 and the second shaft 58 should also be sufficiently rigid such that the surgeon can place the ablation segment 28 of the ablation tool 24 in pressured contact with the tissue treatment site. That is, the first shaft 56 and the second shaft 58 are sufficiently stiff to enable the surgeon to press the ablation segment 28 against the tissue to be treated without inducing a further deformation in the shape of the first shaft 56 and the second shaft 58. The first shaft 56 and the second shaft 58 may in some embodiments deflect slightly, and yet have sufficient stiffness to transfer an effective level of lateral force at their distal end.

In an embodiment, the first shaft 56 and the second shaft 58 are configured so that they are deformable in a single plane, where the first shaft 56 and the second shaft 58 remain substantially rigid in all other planes. For example, the first shaft 56 and the second shaft 58 can be manipulated in a first plane from a first shape to a second shape, wherein the first shaft 48 and the second shaft 56 are sufficiently rigid to retain the second shape. The first shaft 56 and the second shaft 58 also have sufficient rigidity such that the first shaft 56 and the second shaft 58 cannot be manipulated in a second plane orthogonal to the first plane, such that the first shaft 56 and the second shaft 58 are deformable only in the first plane. As such the first shaft 56 and the second shaft 58 are deformable in only one plane.

Figure 10:
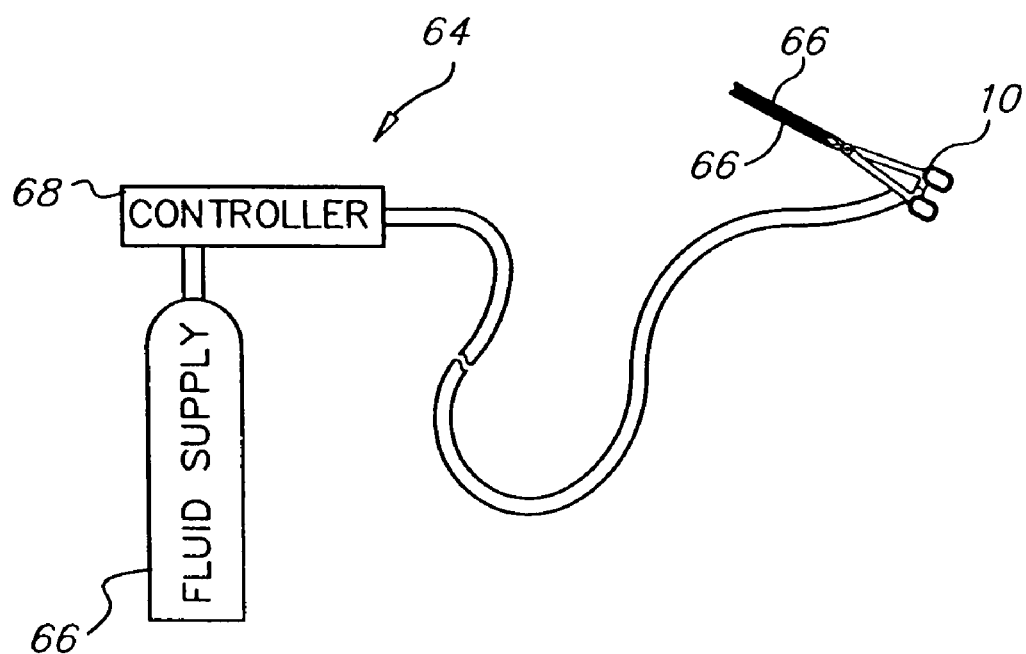
FIG. 10 is a surgical system for operating the surgical clamp in accordance with the present invention.

In an exemplary embodiment, as shown in FIG. 10, the present invention includes an ablation control system 64. The ablation control system 64 includes a supply of cryogenic or cooling fluid 66 in communication with the surgical clamp 10. A fluid controller 68 is interposed or is in-line between the cryogenic fluid supply 66 and the surgical clamp 10 for regulating the flow of cryogenic fluid 66 into the surgical clamp 10 in response to a controller command. Controller commands can include programmed instructions, sensor signals, and manual user input. For example, the fluid controller 68 can be programmed or configured to increase and decrease the pressure of the fluid by predetermined pressure increments over predetermined time intervals.

In another exemplary embodiment, the fluid controller 68 can be responsive to input from a user input device to permit flow of the cryogenic fluid 66 into the surgical clamp 10. As also shown in FIG. 1, one or more temperature elements 40 in electrical communication with the fluid controller 68 can be provided to regulate or terminate the flow of cryogenic fluid 66 into the surgical clamp 10 when a predetermined temperature at a selected point or points on or within the ablation segment 28 is/are obtained. For example a temperature element 40 can be positioned at a point proximate the ablation tool 24 distal end and other temperature elements 40 can be positioned at spaced intervals between the ablation tool 24 distal end and another point that is between the distal end and the proximal end.

In another exemplary embodiment, one or more sensor mechanisms, such as a ECG leads, in electrical communication with the controller can be provided to regulate or terminate the flow of cryogenic fluid 66 into the ablation tool 24 depending on the electrical activity in the tissue being treated. For example, the first elongated jaw 20 and second elongated jaw 22 may provide feedback that permits a user to gauge the completeness of the ablation. Specifically, a lesion blocks electrical signals because it is non-conductive scar tissue. The first elongated jaw 20 and second elongated jaw 22 can be used to measure the ability of the lesion to block an electrical signal. Referring to FIG. 1, an electrode 70 is affixed one each to the distal ends of the first elongated jaw 20 and second elongated jaw 22. In an exemplary use, the electrodes 70 are used to verify electrical isolation of the lesion created by the ablation tool 24. For example, the first elongated jaw 20 and the second elongated jaw 22 are opened to position an electrode 70 on each side of the lesion. An electrical signal is transmitted from one electrode, through the lesion, to the opposite electrode. The lesion is considered electrically isolated if the receiving electrode is electrically silent to the signal.

Alternatively, the electrical sensor mechanisms can be replaced or supplemented with pressure sensors. The pressure sensors can be used to determine when the ablation segment is in physical contact with the tissue to be treated.

The cryogenic fluid can be in a liquid or a gas state, or combination thereof. An extremely low temperature can be achieved within the medical device, and more particularly at the ablation segment by cooling the fluid to a predetermined temperature prior to its introduction into the medical device, by allowing a liquid state cryogenic fluid to boil or vaporize, or by allowing a gas state cryogenic fluid to expand. Exemplary liquids include chlorodifluoromethane, polydimethylsiloxane, ethyl alcohol, HFC's such as AZ-20 (a 50-50 mixture of difluoromethane & pentafluoroethane sold by Allied Signal), and CFC's such as DuPont's Freon. Exemplary gasses include argon, nitrous oxide, and carbon dioxide.

Figure 11:
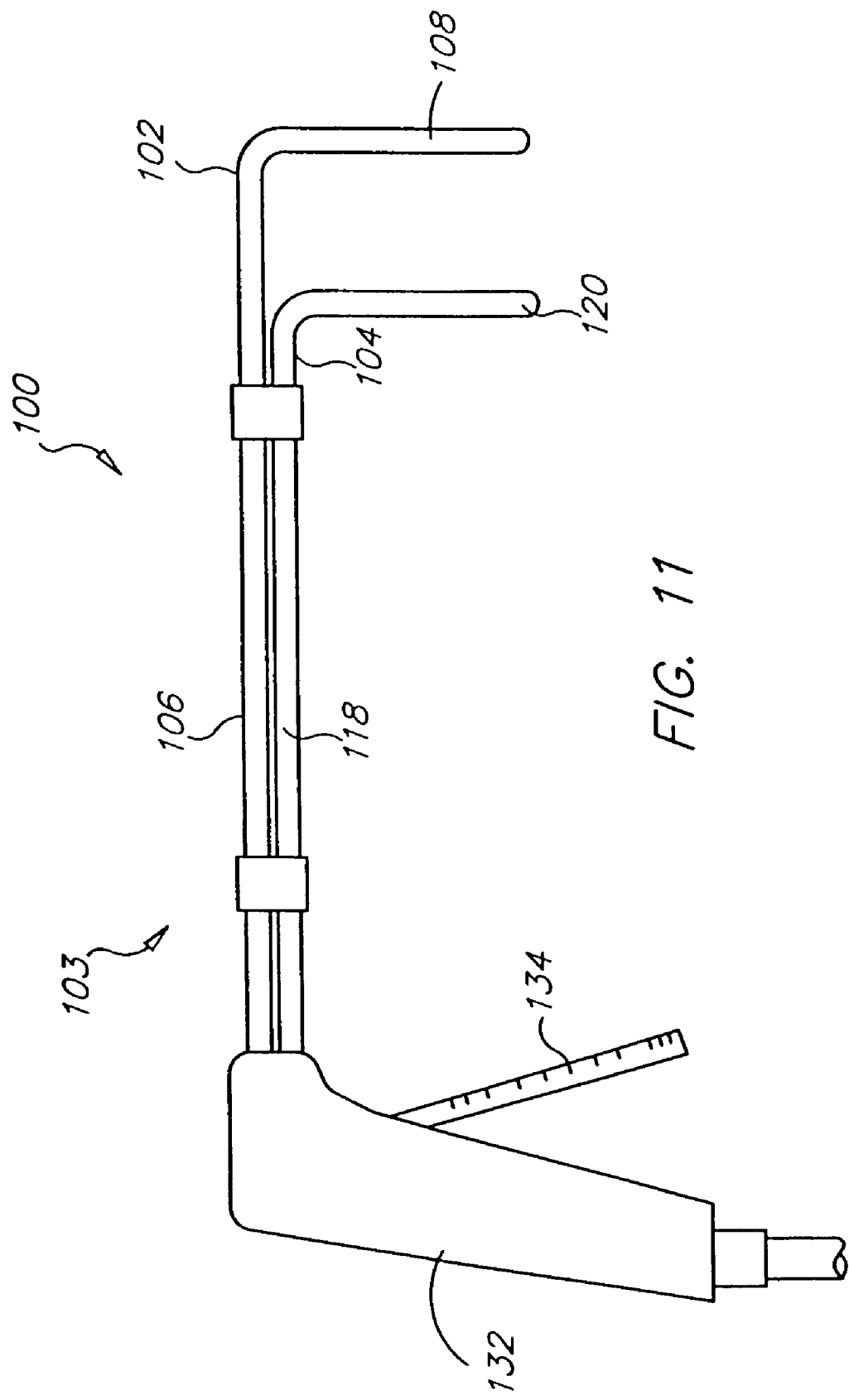
FIG. 11 a plan view of an alternative surgical clamp in accordance with the present invention.

Referring now to FIG. 11, there is shown a plan view of an exemplary embodiment of a medical device constructed in accordance with the principles of the present invention and designated generally as surgical clamp 100. The surgical clamp 100 includes a shaft assembly having opposing jaw assemblies 102, 104 with jaw assembly 102 being fixed and jaw assembly 104 being movable between a first position, wherein the jaw assemblies 102 and 104 are disposed in a spaced apart relation relative to one another, to a second position, wherein the jaw assemblies 102 and 104 cooperate to grasp tissue therebetween.

Figure 12:
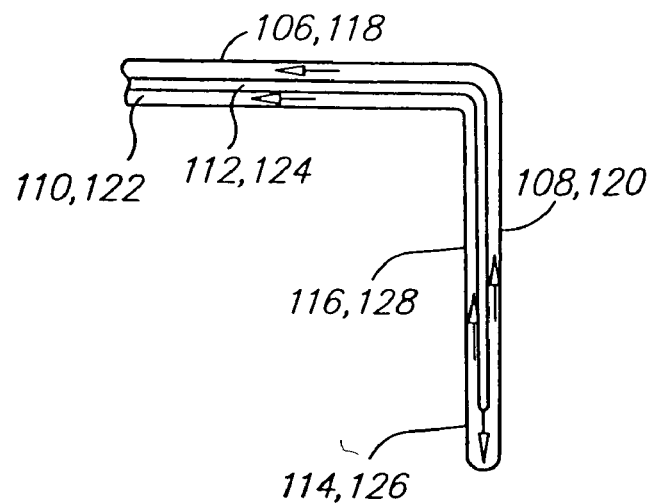
FIG. 12 is a sectional view of an elongated shaft and ablation segment of the surgical clamp of FIG. 11.

The fixed jaw assembly 102 includes a fixed extension shaft 106 and an ablation tool 108 disposed on the distal end of the fixed extension shaft 106, at an acute angle to the fixed extension shaft 106. As shown in FIG. 12, the fixed extension shaft 106 defines a first lumen 110 having at least one input lumen 112 positioned therein, wherein the first lumen 110 and the at least one input lumen 112 define a fluid path to the ablation tool 108, wherein the at least one input lumen 112 is in fluid communication with a cryogenic fluid source. The ablation tool 108 includes an ablation segment 114 with a thermally-transmissive region 116, defines a fluid path through the ablation tool 108 to the ablation segment 112, wherein the fluid path is in fluid communication with the first lumen 110 and the at least one input lumen 112.

The moveable jaw assembly 104 includes a movable extension shaft 118 and a moveable jaw 120 disposed on the distal end of the moveable extension shaft 118 at an acute angle to the moveable extension shaft 118. The moveable extension shaft 118 is operably connected to the fixed extension shaft 106, such that the moveable extension shaft 118 slides along the fixed extension shaft 106 to move the moveable jaw 120 between a first position, wherein the moveable jaw 120 and the ablation tool 108 are disposed in a spaced apart relation relative to one another, to a second position, wherein the moveable jaw 120 and the ablation tool 108 cooperate to grasp tissue therebetween.

In an exemplary embodiment, the ablation tool 108 and the moveable jaw 120 are malleable, each having a shape-holding deformability, that is, they have rigidity such that the ablation tool 108 and the moveable jaw 120 each retain a first shape until manipulated to a further shape with the application of moderate pressure, and until reshaped. The ablation tool 108 and the moveable jaw 120 retain their shape with sufficient rigidity to manipulate the ablation segment 114 against the tissue, and push it past intervening tissue to a desired position.

It is understood that shape, as used herein, is to be construed broadly to include any contour which is needed to configure the ablation tool 108 and the moveable jaw 120 for positioning the active or distal portion of the ablation tool 104, and may include successive bends or segments having more than one curve, angle, deformation or other non-linear configuration. The shape-retaining feature of the ablation tool 108 and the moveable jaw 120 allows an operator to bend the ablation tool 108 and the moveable jaw 120 to a shape or contour, for example around an organ or tissue structure, and have an optimal configuration for positioning and or orienting the active or distal region of the ablation tool 108 and the moveable jaw 120 based upon the particular anatomy of a patient and the location of the treatment site.

Further, the stiffness of the ablation tool 108 and the moveable jaw 120 is such that the surgeon can form the ablation tool 108 and the moveable jaw 120 by hand to a desired shape without undue effort, and yet the ablation tool 108 and the moveable jaw 120 retain the set shape as the surgical clamp 100 is maneuvered to and held in position at the treatment site. The ablation tool 108 and the moveable jaw 120 should also be sufficiently rigid such that the surgeon can place the ablation tool 108 and the moveable jaw 120 in pressured contact with the tissue treatment site. That is, the ablation tool 108 and the moveable jaw 120 are sufficiently stiff to enable the surgeon to press the ablation segment 114 against the tissue to be treated without inducing a further deformation in the shape of the ablation tool 108 and the moveable jaw 120. The ablation tool 108 and the moveable jaw 120 may in some embodiments deflect slightly, and yet has sufficient stiffness to transfer an effective level of lateral force at its distal end.

In an exemplary embodiment, the ablation tool 108 and the moveable jaw 120 are configured so that they are deformable in a single plane, where the ablation tool 108 and the moveable jaw 120 remain substantially rigid in all other planes. For example, the ablation tool 108 and the moveable jaw 120 can be manipulated in a first plane from a first shape to a second shape, wherein the ablation tool 108 and the moveable jaw 120 are sufficiently rigid to retain the second shape. The ablation tool 108 and the moveable jaw 120 also have sufficient rigidity such that the ablation tool 108 and the moveable jaw 120 cannot be manipulated in a second plane orthogonal to the first plane, such that the ablation tool 108 and the moveable jaw 120 are deformable only in the first plane. As such the ablation tool 108 and the moveable jaw 120 are deformable in only one plane.

In an exemplary embodiment, the fixed extension shaft 106 and the moveable extension shaft 118 are malleable, each have a shape-holding deformability, that is, they have a rigidity such that the fixed extension shaft 106 and the moveable extension shaft 118 shaft each retain a first shape until manipulated to a further shape with the application of moderate pressure, and until reshaped. The fixed extension shaft 106 and the moveable extension shaft 118 retain their shape with sufficient rigidity to close the ablation tool 108 and the moveable jaw 120 to grasp the tissue, and push it past intervening tissue to a desired position. The shape-retaining feature of the fixed extension shaft 106 and the moveable extension shaft 118 allows an operator to bend the fixed extension shaft 106 and the moveable extension shaft 118 to a shape or contour, for example around an organ or tissue structure, and have an optimal configuration for positioning and or orienting the active or distal region of the surgical clamp 100 based upon the particular anatomy of a patient and the location of the treatment site.

It is understood that shape, as used herein, is to be construed broadly to include any contour which is needed to configure the fixed extension shaft 106 and the moveable extension shaft 118 for positioning the active or distal portion of the ablation tool 104, and may include successive bends or segments having more than one curve, angle, deformation or other non-linear configuration. The shape-retaining feature of the fixed extension shaft 106 and the moveable extension shaft 118 allows an operator to bend the fixed extension shaft 106 and the moveable extension shaft 118 to a shape or contour, for example around an organ or tissue structure, and have an optimal configuration for positioning and or orienting the active or distal region of the fixed extension shaft 106 and the moveable extension shaft 118 based upon the particular anatomy of a patient and the location of the treatment site.

Further, the stiffness of the fixed extension shaft 106 and the moveable extension shaft 118 is such that the surgeon can form the fixed extension shaft 106 and the moveable extension shaft 118 by hand to a desired shape without undue effort, and yet the fixed extension shaft and the moveable extension shaft retains the set shape as the surgical clamp 100 is maneuvered to and held in position at the treatment site. The fixed extension shaft 106 and the moveable extension shaft 118 should also be sufficiently rigid such that the surgeon can place the ablation segment of the ablation segment 114 in pressured contact with the tissue treatment site. That is, the fixed extension shaft 106 and the moveable extension shaft 118 are sufficiently stiff to enable the surgeon to press the ablation segment 114 against the tissue to be treated without inducing a further deformation in the shape of the fixed extension shaft 106 and the moveable extension shaft 118. The fixed extension shaft 106 and the moveable extension shaft 118 may in some embodiments deflect slightly, and yet has sufficient stiffness to transfer an effective level of lateral force at its distal end.

In an embodiment, the fixed extension shaft 106 and the moveable extension shaft 118 are configured so that they are deformable in a single plane, where the fixed extension shaft 106 and the moveable extension shaft 118 remain substantially rigid in all other planes. For example, the fixed extension shaft 106 and the moveable extension shaft 118 can be manipulated in a first plane from a first shape to a second shape, wherein the fixed extension shaft 106 and the moveable extension shaft 118 are sufficiently rigid to retain the second shape. The fixed extension shaft 106 and the moveable extension shaft 118 also have sufficient rigidity such that the fixed extension shaft 106 and the moveable extension shaft 118 cannot be manipulated in a second plane orthogonal to the first plane, such that the fixed extension shaft 106 and the moveable extension shaft 118 are deformable only in the first plane. As such the fixed extension shaft 106 and the moveable extension shaft 118 are deformable in only one plane.

Referring to FIG. 12, the moveable extension shaft 118 defines a first lumen 122 having at least one input lumen 124 positioned therein, the first lumen 122 and the at least one input lumen 124 defining a fluid path to the moveable jaw 120, wherein the at least one fluid input lumen 124 is in fluid communication with a cryogenic fluid source. The moveable jaw 120 is an ablation tool including an ablation segment 126 with a thermally-transmissive region 128, and defining a fluid path through the moveable jaw 120 to the ablation segment 126, wherein the fluid path is in fluid communication with the first lumen 122 and the at least one input lumen 124.

The fixed jaw assembly 102 and the moveable jaw 104 assembly are operably connected to a handle assembly 103. The handle assembly 103 includes a fixed handle 132 attached to the fixed extension shaft 106 and a lever arm 134 pivotally connected to the fixed handle 132. The lever arm 134 is attached to the movable extension shaft, 118 such that as the lever arm 134 pivots about the fixed handle 132 from a start position, the moveable jaw 120 moves from a first position to a second position.

Figure 13:
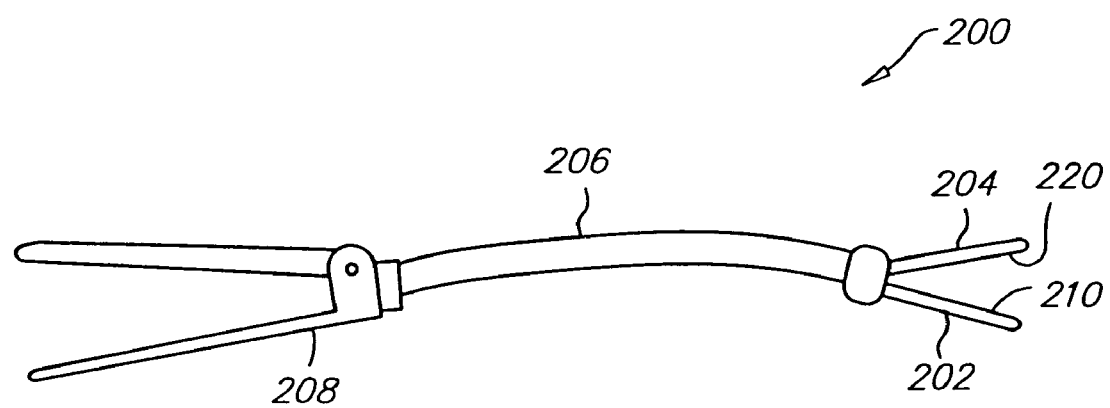
FIGS. 13-17 illustrate additional configurations of a surgical clamp.

Referring now to FIG. 13, there is shown a plan view of an exemplary embodiment of a medical device constructed in accordance with the principles of the present invention and designated generally as surgical clamp 200. The surgical clamp 200 includes a jaw assembly having a first jaw 202, and a second jaw 204 in opposing relation. The first jaw 202 and the second jaw 204 are movable between a first position, wherein the first jaw 202 and the second jaw 204 are disposed in a spaced apart relation relative to one another, to a second position, wherein the first jaw 202 and the second jaw 204 cooperate to grasp tissue therebetween. The first jaw 202 and the second jaw 204 are connected to an elongated shaft assembly 206, wherein a handle assembly 208 is connected to the elongated shaft assembly 206 opposite the first jaw 202 and the second jaw 204. At least one of the first jaw 202 and the second jaw 204 includes an ablation tool. For example, the first jaw 202 includes an ablation tool 210 positioned on the inner surface 212 of the first jaw 202.

The elongated shaft assembly 206 defines a first lumen having at least one input lumen positioned therein (not shown). The first lumen and the at least one input lumen define a fluid path to the ablation tool 210, wherein the at least one input lumen is in fluid communication with a cryogenic fluid source. The ablation tool 210 includes an ablation segment with a thermally-transmissive region, and defines a fluid path through the ablation tool to the ablation segment, wherein the fluid path is in fluid communication with the first lumen and the at least one input lumen.

Additionally, the second jaw 204 can include an ablation tool 220 having an ablation segment with a thermally-transmissive region similar to that of ablation tool 210 disposed on first jaw 202.

In an exemplary embodiment, the first jaw 202 and the second jaw 204 are malleable, each have a shape-holding deformability, that is, they have rigidity such that the first jaw 202 and the second jaw 204 each retain a first shape until manipulated to a further shape with the application of moderate pressure, and until reshaped. The first jaw 202 and the second jaw 204 retain their shape with sufficient rigidity to manipulate the ablation segment 210 against tissue, and push it past intervening tissue to a desired position.

It is understood that shape, as used herein, is to be construed broadly to include any contour which is needed to configure the first jaw 202 and the second jaw 204 for positioning the active or distal portion of the ablation tool, and may include successive bends or segments having more than one curve, angle, deformation or other non-linear configuration. The shape-retaining feature of the first jaw 202 and the second jaw 204 allows an operator to bend the first jaw 202 and the second jaw 204 to a shape or contour, for example around an organ or tissue structure, and have an optimal configuration for positioning and or orienting the active or distal region of the first jaw 202 and the second jaw 204 based upon the particular anatomy of a patient and the location of the treatment site.

Further, the stiffness of the first jaw 202 and the second jaw 204 is such that the surgeon can form the first jaw 202 and the second jaw 204 by hand to a desired shape without undue effort, and yet the first jaw 202 and the second jaw 204 retain the set shape as the surgical clamp 200 is maneuvered to and held in position at the treatment site. The first jaw 202 and the second jaw 204 should also be sufficiently rigid such that the surgeon can place the ablation segment of the ablation tool in pressured contact with the tissue treatment site. That is, the first jaw 202 and the second jaw 204 are sufficiently stiff to enable the surgeon to press the ablation segment against the tissue to be treated without inducing a further deformation in the shape of the first jaw 202 and the second jaw 204. The first jaw 202 and the second jaw 204 may in some embodiments deflect slightly, and yet have sufficient stiffness to transfer an effective level of lateral force at its distal end.

In an exemplary embodiment, the first jaw 202 and the second jaw 204 are configured so that they are deformable in a single plane, where the first jaw 202 and the second jaw 204 remain substantially rigid in all other planes. For example, the first jaw 202 and the second jaw 204 can be manipulated in a first plane from a first shape to a second shape, wherein the first jaw 202 and the second jaw 204 are sufficiently rigid to retain the second shape. The first jaw 202 and the second jaw 204 also have sufficient rigidity such that the f first jaw 202 and the second jaw 204 cannot be manipulated in a second plane orthogonal to the first plane, such that the first jaw 202 and the second jaw 204 are deformable only in the first plane. As such the first jaw 202 and the second jaw 204 are deformable in only one plane.

In an exemplary embodiment, the elongated shaft assembly 206 is malleable, having a shape-holding deformability, that is, it has rigidity such that the elongated shaft assembly 206 retains a first shape until manipulated to a further shape with the application of moderate pressure, and until reshaped. The elongated shaft assembly 206 retains its shape with sufficient rigidity to close the first jaw 202 and the second jaw 204 to grasp the tissue, and push it past intervening tissue to a desired position.

It is understood that shape, as used herein, is to be construed broadly to include any contour which is needed to configure the surgical clamp 200 for positioning the active or distal portion of the ablation tool, and may include successive bends or segments having more than one curve, angle, deformation or other non-linear configuration. The shape-retaining feature of the elongated shaft assembly 206 allows an operator to bend the elongated shaft assembly 206 to a shape or contour, for example around an organ or tissue structure, and have an optimal configuration for positioning and or orienting the active or distal region of the surgical clamp 200 based upon the particular anatomy of a patient and the location of the treatment site.

Further, the stiffness of the elongated shaft assembly 206 is such that the surgeon can form the elongated shaft assembly 206 by hand to a desired shape without undue effort, and yet the elongated shaft assembly 206 retains the set shape as the surgical clamp 200 is maneuvered to and held in position at the treatment site. The elongated shaft assembly 206 should also be sufficiently rigid such that the surgeon can place the ablation segment of the ablation tool in pressured contact with the tissue treatment site. That is, the elongated shaft assembly 206 is sufficiently stiff to enable the surgeon to press the ablation segment against the tissue to be treated without inducing a further deformation in the shape of the elongated shaft assembly 206. The elongated shaft assembly 206 may in some embodiments deflect slightly, and yet has sufficient stiffness to transfer an effective level of lateral force at its distal end.

In an embodiment, the elongated shaft assembly 206 is configured so that it is deformable in a single plane, where the elongated shaft assembly 206 remains substantially rigid in all other planes. For example, the elongated shaft assembly 206 can be manipulated in a first plane from a first shape to a second shape, wherein the elongated shaft assembly 206 is sufficiently rigid to retain the second shape. The elongated shaft assembly 206 also has sufficient rigidity such that the elongated shaft assembly 206 cannot be manipulated in a second plane orthogonal to the first plane, such that the elongated shaft assembly 206 is deformable only in the first plane. As such the elongated shaft assembly 206 are deformable in only one plane.

Figure 14:
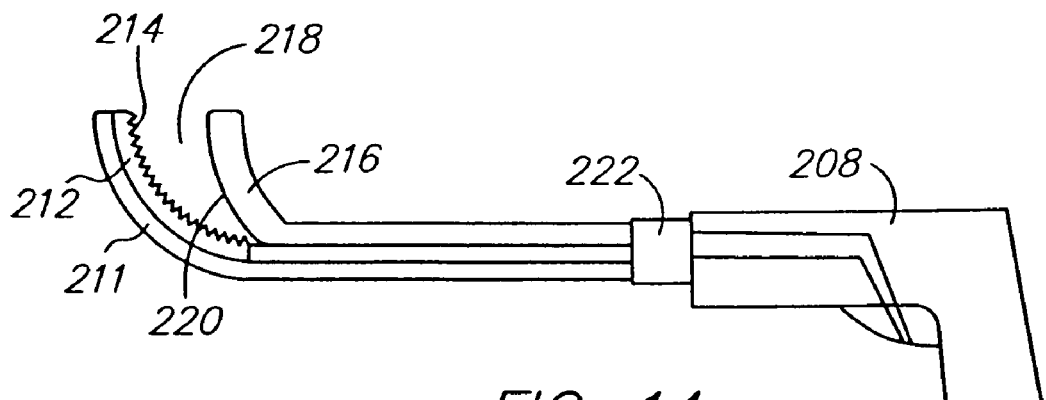

Referring now to FIG. 14, an exemplary tool is shown having a handle portion 208 from which extends a probe 211 having a cooling segment 212. As with all disclosed embodiments, the cooling segment 212 can be provided with a smooth or textured tissue engaging surface 214. In FIG. 14, the tissue-engaging surface 214 is textured to have "teeth." A second element 216 is movable relative to the probe to define a tissue capture zone 218. A distal region 220 of the second element 216 can have a complementary shape to the cooling segment 212 and be smooth (as shown) or textured. As the probe 211 and the second element 216 are moved axially with respect to each other, the tissue capture zone 218 increases or decreases in size. In the illustrated embodiment, the second element 216 is secured to the probe 211 and is axially slidable with respect thereto by axially moving a proximal portion 222 of the second element 216.

Figure 15:
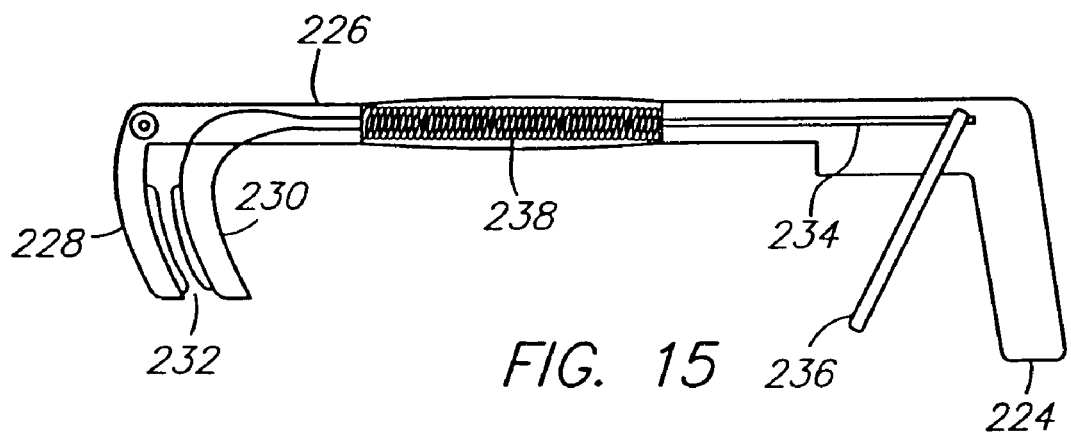

With respect to FIG. 15, a different actuating mechanism is shown in an exemplary tool having a handle portion 224 from which extends a probe 226 having a cooling segment 228. A second element 230 is movable relative to the probe 226 to define a tissue capture zone 232. As the probe 226 and the second element 230 are moved axially with respect to each other, the tissue capture zone 232 increases or decreases in size. In the illustrated embodiment, the second element 230 is secured to the probe 226 and is axially slidable with respect thereto by axially moving a proximal portion 234 of the second element by pulling a handle, lever, or trigger 236 that is engaged with the proximal portion of the second element. A spring 238 or other bias means can be provided to either urge the second element 230 in either the distal or proximal direction.

Figure 16:
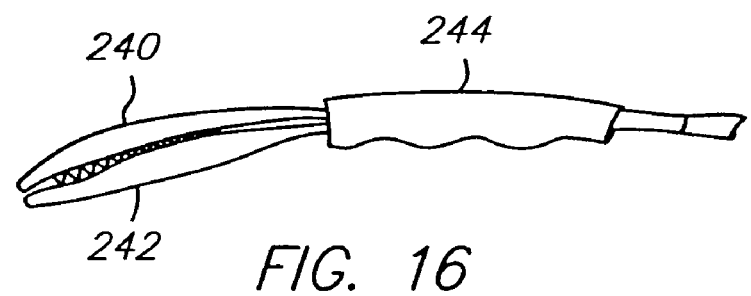

FIG. 16 shows yet another configuration wherein a cooling element 240 is juxtaposed with a second element 242 and wherein the elements are biased apart. A sleeve or handle element 244 is slidable with respect to the elements so that as it is moved distally it urges the elements together.

Figure 17:
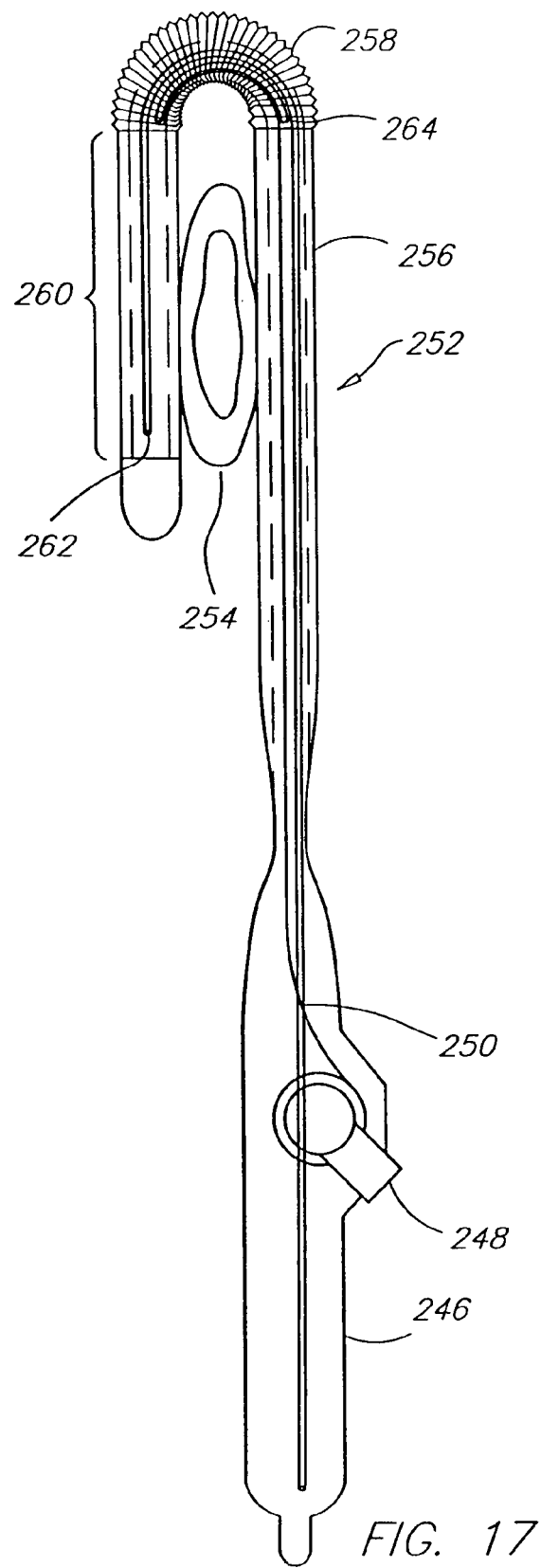

Referring to FIG. 17 another clamping tool is disclosed that includes a handle portion 246 having an actuator 248 that pivots or rotates fore and aft. The actuator 248 is coupled to a pull or push wire 250 that is secured to a distal portion of an elongate shaft structure 252 to cause the shaft structure to clamp tissue 254. As shown, the shaft structure 252 includes an insulating distal portion 256, a bellows or coil portion 258 that provides a clamping effect, and a cooling segment 260. A coolant injection tube 262 introduces coolant into the cooling segment 260. The elongate shaft structure 252 can be transitioned from a substantially linear configuration to the configuration shown or it can be preformed to substantially the configuration shown and actuated to tighten the space between the insulating distal portion 256 and the cooling segment 260 which can further be insulated on its outward face. As shown, the wire 250 is secured at its distal end to a shim 264.

FIG. 18 illustrates yet another configuration of a tool including a handle 266, actuator 268, insulated shaft 270, first jaw 272, and second jaw 274, wherein manipulation of the actuator 268 causes the jaws to open and close or move relative to each other. The figure depicts the jaws in both the open and clamped state. Coolant can flow to and/or through one or both jaws and both jaws can be insulated except at the point where they meet. One or both jaws can be provided with temperature and/or impedance measurement devices to monitor and evaluate lesion formation and characteristics. In an embodiment a temperature sensor is associated with a jaw that does not have a cooling element. The jaws are clamped together with tissue therebetween. The transmurality of a lesion could be ascertained when the temperature sensor detects a temperature of −40 degrees Centigrade for two minutes. Of course time and temperature may be different for different types, conditions and thickness of tissue.

FIGS. 19 and 20 show additional details of the first jaw 272 and the second jaw 274, respectively; wherein the first jaw made of an insulating material defines a recess 276 shaped to receive an elongate cooling element 278 affixed to insulating material. The cooling element 278 may be removable from the jaw elements. The cooling element 278 maybe inserted and retained in place on one of the jaws. An ablation of tissue maybe performed by placing the jaws of the medical device around the tissue and activating an ablation element. Upon completion of the ablation, the cooling element may be removed from the jaw and the medical device may be used as a "wand-like" device to perform additional procedures.

In an alternate embodiment, one of the two jaws can be removable so that a single jaw with an active element, for example the ablation or cooling element, is provided. Thus, the device can be convertible from a clamping tool to a "wand" type device for use in procedures not requiring clamping.

Figure 21:
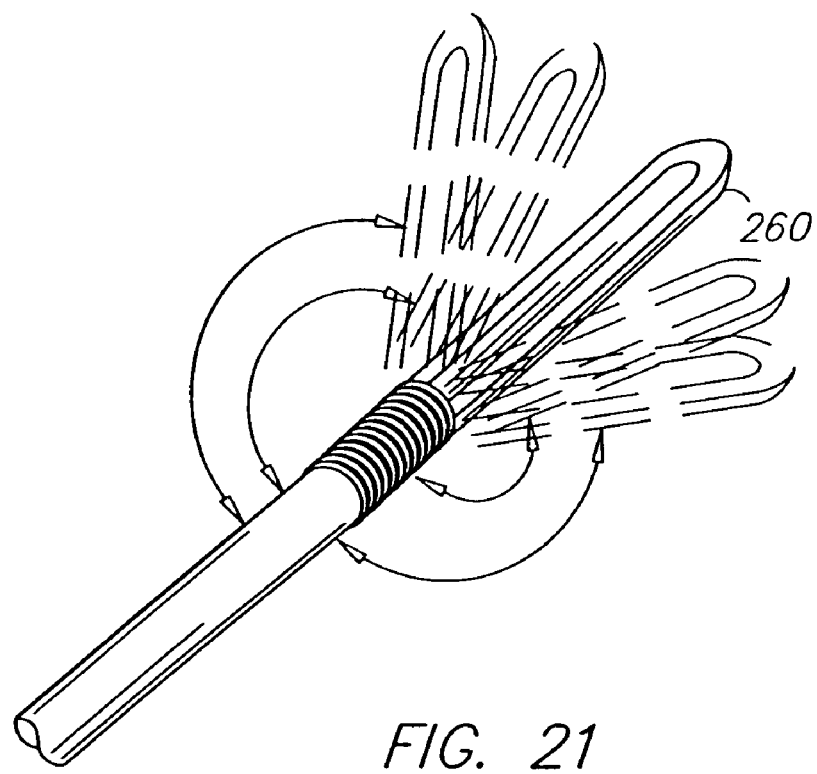
FIGS. 21 and 22 show additional clamp configurations.

FIG. 21 illustrates yet another configuration for the clamping device. Here, cooling segment 260 can be deflected from its normal position to a variety of deflection positions via use of actuator 248 (not shown). Cooling segment 260 may be deflected to an angle of choice by manipulation of the actuator. Coolant can then be introduced to cooling segment 260 via the internal injection tube (not shown).

Figure 22:
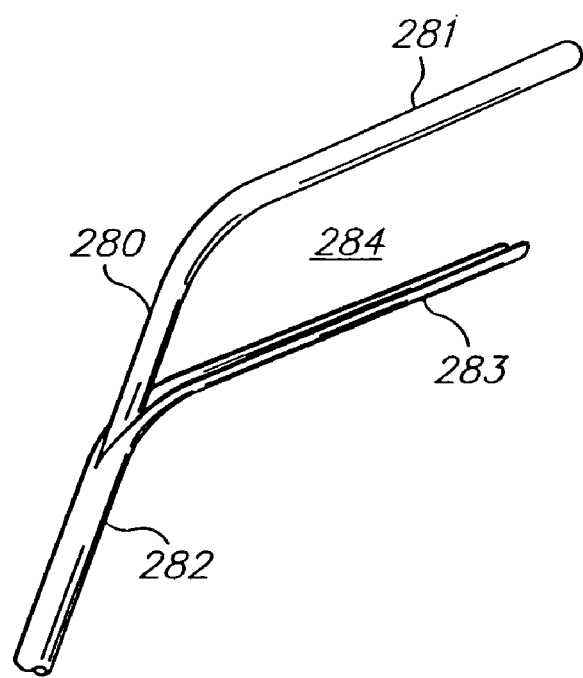

FIG. 22 illustrates yet another configuration for a clamping device wherein a cooling element 280 is slidably disposed within an insulating sheath 282. The distal portion of the cooling element 281 and the distal portion of the sheath 283 are angled with respect to their proximal portion so that extension and retraction of the cooling element with respect to the sheath opens and closes a tissue-clamping zone 284.

Although generally shown as a cryogenic ablation tool, it is understood that in other embodiments the ablation segment applies other types of energy or combination of energies, to the tissue to be treated, including, but not limited to, cryogenic energy, radio frequency (RF) energy, microwave energy, ultrasound energy, laser energy, and contact heating energy. It is further understood that other devices can be coupled to the guide distal end, for example, cameras, video devices, probes and other components can be affixed to the guide for various applications. For example, pacing/sensing electrodes can be affixed to points on the slotted segment.

The medical device of the present invention is well suited for treating tissue in a variety of locations in the body during invasive surgical procedures. Illustrative applications include open thoracic and peritoneal surgery as well as endoscopic procedures, e.g., treating tissue located at or near the heart, intestines, uterus, and other regions for which surgical or endoscope assisted surgical access and topical tissue treatment, or cauterization or ablation is appropriate, as well as ophthalmic surgery, and tumor ablation and various applications preparatory to further surgical steps.

Figure 23:
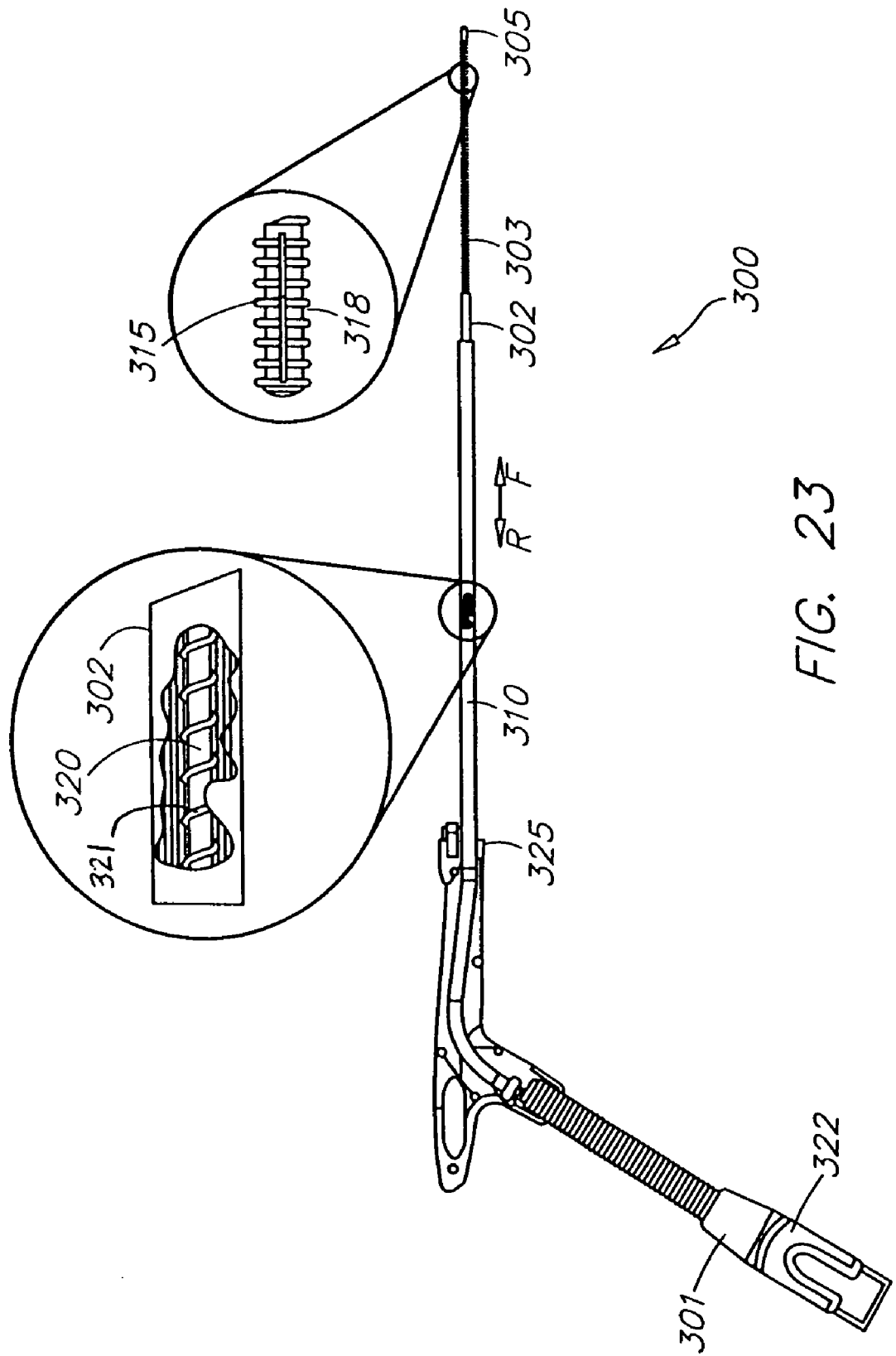
FIG. 23 illustrates a wand-type cryoprobe.

FIG. 23 illustrates a wand-type cryoprobe. The probe 300 includes a handle portion 301 and a manually deformable main shaft 302. The shaft 302 includes a malleable and deformable distal section 303, having a bellows-shaped configuration that may be made of convoluted stainless steel tubing. At the very distal tip of the distal section 303 is a tip extension 305 for use with suture during surgical procedures. The tip extension 305 may include a hollow section and a solid section. The solid section the tip extension 305 may have a drilled hole or eyelet with a small diameter of, for example, 0.05 to 0.09 inch, which is adapted for receiving a wire or other suitable device (not shown); and provides the operator or physician the capability of grasping and manipulating the probe around the target tissue. The edges of this hole or eyelet are rounded in order to prevent severing the wire or other suitable device.

The probe 300 further includes a slidable insulation sheath 310 disposed over the central portion of the main shaft 302, adapted to slide along the direction of the arrows F and R as shown in the figure. The sheath 310 can slide over varying lengths of the distal section 303, to cover up portions of the distal section and thereby insulate said portions from heat transfer.

Coolant enters the probe through a central injection tube 315, which extends to the distal tip 305 and includes at least one exit point (for example, at least one nozzle) proximate the distal tip 305. A temperature sensor mechanism 318 is included proximate the exit point of the injection tube 315 to measure the temperature of fluid exiting the tube, and to render a measure of the overall temperature around the tip of the probe 300. In this exemplary embodiment, the injection tube 315 runs concentrically within an outer tube (not numbered) thereby forming a return space surrounding the injection tube 315 and extending back to the fluid connector 322. A heat exchanger 320 is also included along the injection tubing as shown, inside the shaft 302. The heat exchanger 320 includes a portion of the injection tubing 315 and a small diameter thermally conductive wire 321, for example solid copper, which is coiled or wound around the portion of injection tubing 315. After the cooling fluid is provided to the thermally-transmissive region of the distal tip 305, and injected into the tip, the spent vapor is returned through the return space where it flows over the heat exchanger to subcool the cooling fluid in the portion of the injection tubing 315. Subcooling of the cooling fluid may prevent the formation of gas bubbles in the cooling fluid prior to injection into the distal tip 305. The handle portion includes a quick-connecting high-pressure line and port 322 to provide a means of supplying and evacuating refrigerant from the device. An alternate temperature reading connector 325 is also provided for connection with a plug disposed on the surgical clamp disclosed in FIG. 24 below.

Figure 24:
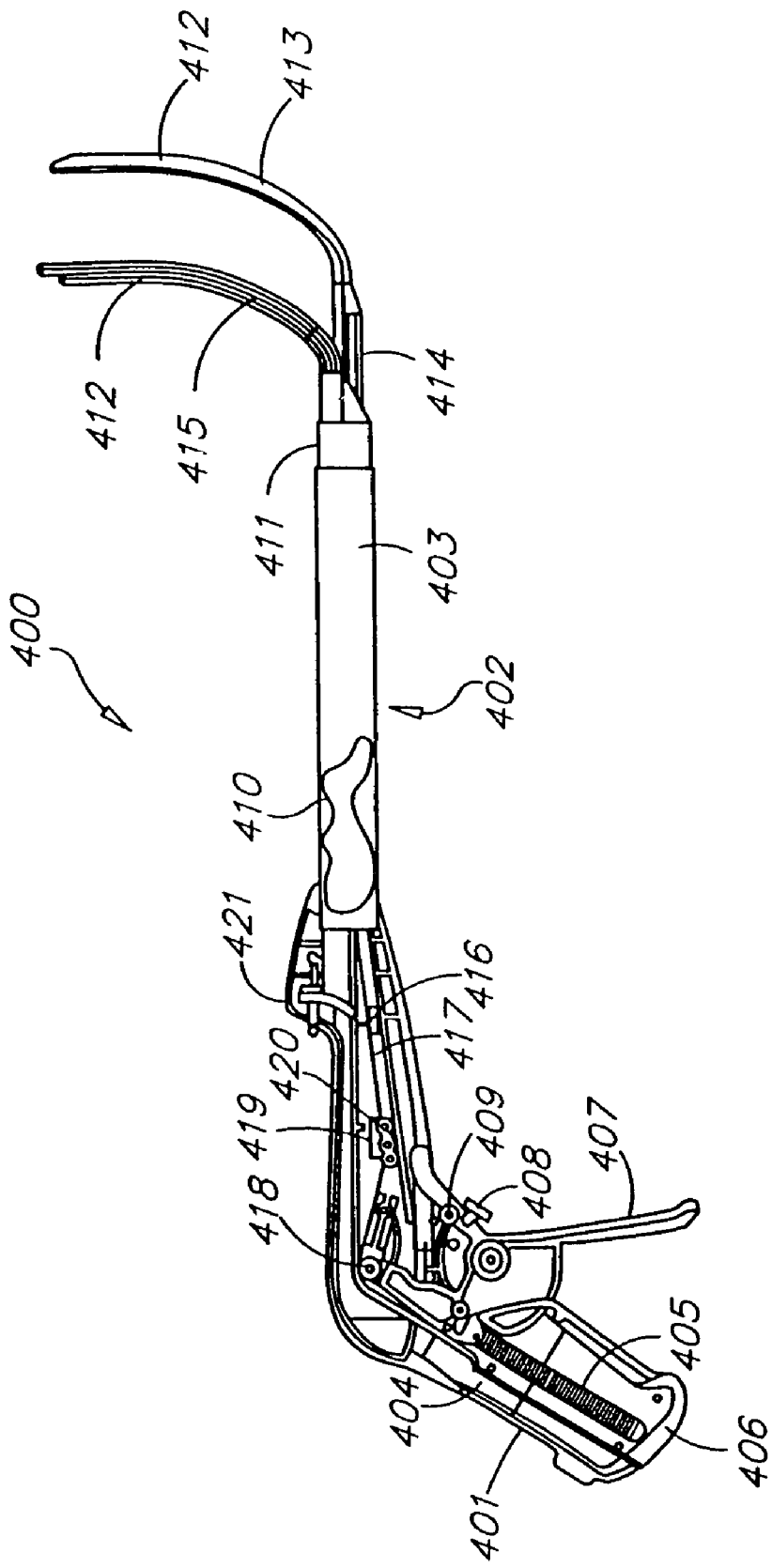
FIG. 24 illustrates an additional surgical clamp adapted to be used in conjunction with the wand-type probe shown in FIG. 23.

FIG. 24 illustrates a surgical clamp 400 adapted to be used in conjunction with the wand-type probe 300 shown in FIG. 23. Clamp 400 includes a handle portion 401 and a main shaft 402. Handle portion 401 includes a handle housing 404 that encloses a trigger extension spring 405, with a handle pin 406 at the proximal end of spring 405. Trigger 407 is pivotally coupled to handle 401. Trigger lock 408 and trigger pin 409 act to prevent the unintentional activation of the trigger.

Main shaft 402 extends from handle portion 401 and is covered by a protective sleeve 403. Main shaft 402 includes a tightly-wound main coil 410 and a proximal jaw 411 from which extend a pair of thermocouple sensors 412. Main coil 410 provides flexibility and malleability to main shaft 402. The distal sensor includes a distal reinforcement element 413 and a distal jaw 414. The proximal sensor includes a proximal reinforcement element 415.

A mobile spring 416 provides the linkage between handle portion 401 and main shaft 402. Mobile spring 416 is enclosed by protective sleeve 417. Linkage 418 provides the mechanical interface between the trigger 407 and main shaft 402 in addition to thermocouple wire 419 coupled to spring attachment 420. An alternate temperature reading miniature plug 421 is also included in order to measure the average temperature of the ablation site and the temperature opposite the ablation site. Plug 421 is used in conjunction with an alternate temperature recording device to provide accurate readings from each temperature sensor 412. Plug 421 and associated switching circuitry enables one temperature sensor while disabling the other thereby guaranteeing the recording from only one temperature sensor at a time.

Figure 25:
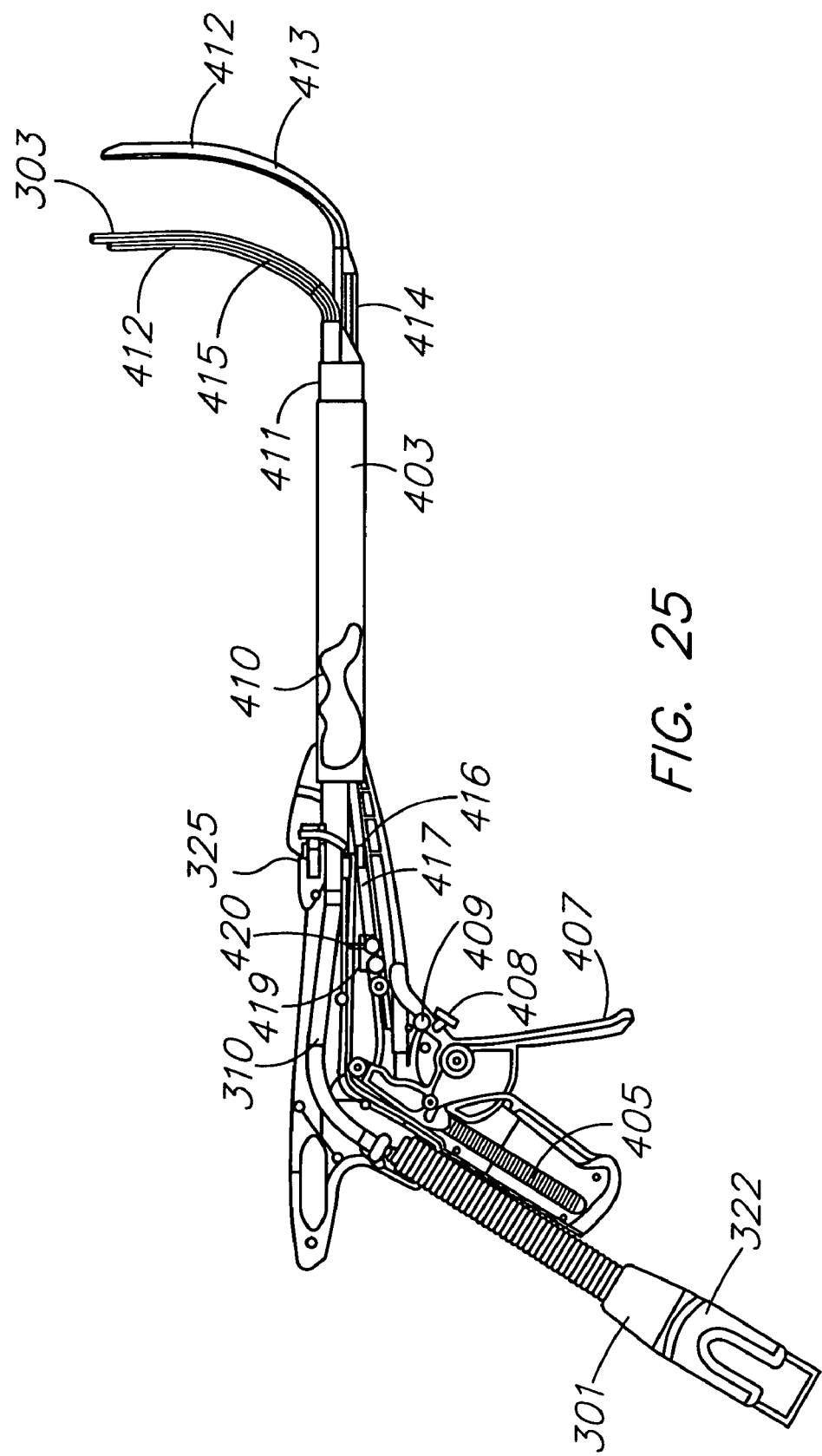
FIG. 25 illustrates the probe of FIG. 23 and clamp of FIG. 24 assembled together.

FIG. 25 illustrates the probe 300 of FIG. 23 assembled together with the clamp 400 of FIG. 24. Sensors 412 are used for transmurality assessment of lesions by measuring the temperature and/or impedance of the tissue between the jaws of the clamp. Two illustrative examples of a sensor used in connection with the present invention are shown in FIGS. 26A and 26B.

FIGS. 26A and 26B illustrate two embodiments of a transmurality assessment mechanism disposed on an ablation device such as a cryoprobe or surgical clamp. Typically, one or more sensor mechanisms, having one or more sensor electrodes 422, may be disposed on one or more jaws 423 of the ablation device. Sensor electrodes 422 can measure temperature of the opposing jaw and/or impedance of the tissue being treated between opposing jaws of the ablation device. The resulting temperature or impedence readings provide an indication of the transmurality of the lesion. Alternatively, the impedance sensor electrodes 422 may be disposed on one jaw or both jaws to measure the existence of ice formation in the tissue or the propagation of ice in the tissue.

FIG. 27 illustrates one embodiment of the surgical clamp of the present invention. The embodiment of FIG. 27 represents a hinged surgical clamp having active cryotreatment elements. Probe 427 includes two jaws, a passive, mobile jaw 424 and a stationary, active jaw 428. Passive jaw 424 is mobile and is controlled by a pull wire actuation mechanism 425. Mechanism 425 controls the rotation of jaw 424 about hinge 426. Pull wire actuation mechanism 425 is covered by protective insulation sleeve 429. FIG. 27 provides an illustration of one type of jaw arrangement for a cryoprobe that provides controlled rotary movement of the jaws in order to properly position the cryoprobe at the target tissue.

FIG. 28 illustrates an alternate embodiment of a hinged surgical clamp having active cryotreatment elements. In this embodiment, passive jaw 424 is of a different shape and size than the jaw depicted in FIG. 27. Passive jaw 424 includes sensing elements and can rotate about hinge 426 and is again controlled by a pull wire actuation mechanism 425 within sleeve 429. Actuation mechanism 425 may include a force limiting spring or latch that creates a space between passive jaw 424 and active jaw 428 to prevent the user from over-squeezing actuation mechanism 425. Actuation mechanism 425 may be coupled to a device that controls the movement of passive jaw 425 such as an on/off switch, a joystick, or one or more motors controlled by a remote control unit.

FIG. 29 illustrates another embodiment of a surgical clamp having a detachable passive jaw. Passive jaw 424 includes temperature sensing elements for transmurality assessment. Jaw 424 is also removable and can be detached from the probe. Active jaw 428 is supported by a removable stiffening member 430, which provides rigidity. A safety gap 431 is formed between jaw 424 and jaw 428 in order to prevent over-squeezing of actuation mechanism 425.

Figure 30:
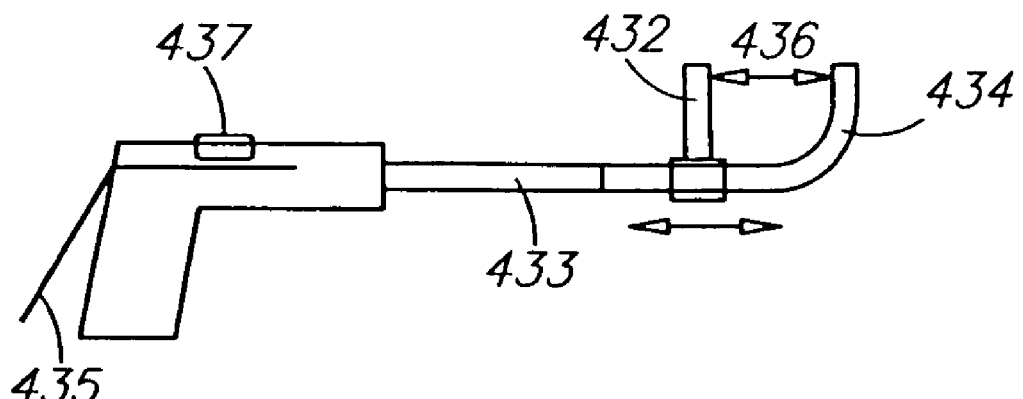
FIG. 30 illustrates another surgical clamp having a sliding jaw.

FIG. 30 illustrates yet another embodiment of the surgical clamp of the present invention. The clamp depicted in FIG. 30 includes a mobile, passive jaw 432 that slides along a flexible shaft 433 while active jaw 434 remains fixed. Mobile jaw 432 can be spring loaded and controlled via an actuation member 435 and an on/off switch 437. Mobile jaw 432 can be controlled to slide along shaft 433 relative to fixed active jaw 434 in order to increase or decrease the clamping gap 436 between the opposing jaws. Mobile jaw 432 includes one or more thermocouples, either separated or along one common support, to provide transmurality feedback. All of the external members are removable and the active jaw may be used as a linear ablation device.

Figure 31:
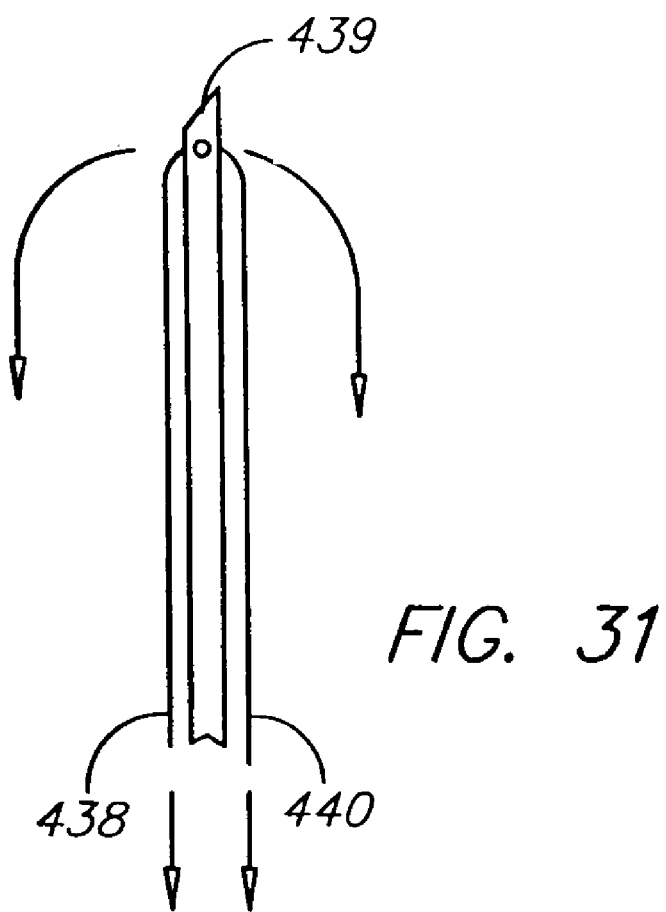
FIG. 31 shows a pull-wire actuated deflection mechanism used in conjunction with a surgical tool to achieve a clamping effect.

FIG. 31 illustrates still another embodiment of the present invention that includes a pull-wire actuated deflection mechanism used in conjunction with a surgical tool to achieve a clamping effect. In this embodiment, two pull-wires 438 and 440 provide a non-symmetric bi-directional clamping mechanism. The pull-wires can be manipulated to deflect jaw 439 in a particular direction. Jaw 439 folds downward and clamps down around the target tissue.

It will be appreciated by persons skilled in the art that the present invention is not limited to what has been particularly shown and described hereinabove. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device, comprising:
   a cryotreatment instrument; and
   a guide element releasably engageable with at least a portion of the cryotreatment element, the guide element including a first jaw, a second jaw, and a channel for receiving at least a portion of the cryotreatment instrument therein, wherein at least a segment of at least one of the first and second jaws pivots about a hinge.

2. The medical device according to claim 1, wherein the guide element includes a first handle portion.

3. The medical device according to claim 2, wherein the first handle portion defines a recess in communication with the channel.

4. The medical device according to claim 2, wherein the first handle portion includes a retention element engageable with the cryotreatment instrument.

5. The medical device according to claim 2, wherein the cryotreatment instrument defines a second handle portion and a cryotreatment element coupled to the second handle portion.

6. The medical device according to claim 5, wherein the second handle portion is releasably engageable with the first handle portion.

7. The medical device according to claim 5, wherein the second handle portion includes a port for coupling to a refrigerant source.

8. The medical device according to claim 5, wherein the cryotreatment element is malleable.

9. The medical device according to claim 5, wherein the cryotreatment element defines a fluid flow path therein.

10. The medical device according to claim 9, wherein the fluid flow path includes an injection tube and an exhaust lumen.

11. The medical device according to claim 10, wherein the fluid flow path further includes a heat exchanger.

12. The medical device according to claim 11, wherein the heat exchanger includes a thermally-conductive wire wound around at least a portion of the injection tube.

13. The medical device according to claim 9, further comprising a temperature sensor in fluid communication with the fluid flow path.

14. The medical device according to claim 5, further comprising a cryogenic fluid supply in fluid communication with the cryotreatment element.

15. The medical device according to claim 14, further comprising an ablation control system in communication with the cryogenic fluid supply.

16. The medical device according to claim 5, wherein the cryotreatment element includes a bellows-shaped region.

17. The medical device according to claim 5, further comprising a sleeve movably positionable along a length of the cryotreatment element.

18. The medical device according to claim 5, wherein the cryotreatment element includes a distal tip defining an eyelet therein.

19. The medical device according to claim 1, wherein the guide element includes a trigger mechanism, wherein activation of the trigger mechanism causes at least one of the first and second jaws to move.

20. The medical device according to claim 19, wherein the guide element includes a trigger lock to releasably lock the trigger mechanism in a fixed position.

21. The medical device according to claim 19, wherein only the distal jaw moves in response to actuation of the trigger mechanism.

22. The medical device according to claim 1, wherein the guide element includes a force limiting mechanism coupled to at least one of the first and second jaws for preventing tissue damage.

23. The medical device according to claim 1, wherein the first jaw defines a recess therein for receiving a portion of the cryotreatment instrument.

24. The medical device according to claim 23, wherein the second jaw defines a substantially planar face opposite the recess of the first jaw.

25. The medical device according to claim 1, further comprising a sensor coupled to at least one of the first and second jaws.

26. The medical device according to claim 25, wherein the sensor is a thermocouple.

27. The medical device according to claim 25, wherein the sensor is a transmurality assessment sensor.

28. The medical device according to claim 27, wherein the transmurality assessment sensor is an impedance sensor.

29. The medical device according to claim 1, further comprising an ECG lead coupled to at least one of the first and second jaws.

* * * * *

UNITED STATES PATENT AND TRADEMARK OFFICE
CERTIFICATE OF CORRECTION

Page 1 of 1

PATENT NO. : 7,981,110 B2
APPLICATION NO. : 11/709067
DATED : July 19, 2011
INVENTOR(S) : Dan Wittenberger et al.

It is certified that error appears in the above-identified patent and that said Letters Patent is hereby corrected as shown below:

In Column 18, at Line 22, change "cryotreatment element" to --cryotreatment instrument--.

Signed and Sealed this
Twenty-seventh Day of December, 2011

David J. Kappos
*Director of the United States Patent and Trademark Office*